(12) United States Patent
Gough et al.

(10) Patent No.: US 7,248,912 B2
(45) Date of Patent: Jul. 24, 2007

(54) TISSUE IMPLANTABLE SENSORS FOR MEASUREMENT OF BLOOD SOLUTES

(75) Inventors: David A. Gough, Cardiff, CA (US); Michael C. Jablecki, La Jolla, CA (US); Joseph Y. Lucisano, San Diego, CA (US); Mark B. Catlin, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 434 days.

(21) Appl. No.: 10/698,911

(22) Filed: Oct. 31, 2003

(65) Prior Publication Data

US 2005/0059871 A1    Mar. 17, 2005

Related U.S. Application Data

(60) Provisional application No. 60/423,220, filed on Oct. 31, 2002.

(51) Int. Cl.
*A61B 5/00*    (2006.01)

(52) U.S. Cl. ........................ 600/347; 600/316; 600/345
(58) Field of Classification Search .................. 600/365
See application file for complete search history.

(56) References Cited

U.S. PATENT DOCUMENTS

| 4,484,987 A | 11/1984 | Gough | |
|---|---|---|---|
| 4,650,547 A | 3/1987 | Gough | |
| 4,671,288 A | 6/1987 | Gough | |
| 4,746,218 A * | 5/1988 | Lord, III | 356/437 |
| 4,748,562 A * | 5/1988 | Miller et al. | 600/350 |
| 4,890,620 A | 1/1990 | Gough | |
| 5,077,476 A * | 12/1991 | Rosenthal | 250/339.04 |
| 5,322,063 A | 6/1994 | Allen et al. | |
| 5,660,163 A | 8/1997 | Schulman et al. | |
| 5,695,623 A * | 12/1997 | Michel et al. | 204/403.05 |
| 5,711,861 A * | 1/1998 | Ward et al. | 600/347 |
| 6,107,083 A * | 8/2000 | Collins et al. | 435/288.7 |
| 6,119,208 A * | 9/2000 | White et al. | 711/162 |
| 6,551,252 B2 * | 4/2003 | Sackner et al. | 600/536 |
| 6,832,114 B1 * | 12/2004 | Whitehurst et al. | 607/40 |
| 2002/0026108 A1 * | 2/2002 | Colvin, Jr. | 600/316 |
| 2002/0156355 A1 * | 10/2002 | Gough | 600/345 |
| 2002/0161286 A1 * | 10/2002 | Gerber et al. | 600/310 |
| 2003/0126593 A1 * | 7/2003 | Mault | 725/10 |
| 2004/0158194 A1 * | 8/2004 | Wolff et al. | 604/66 |
| 2005/0196322 A1 * | 9/2005 | Truex et al. | 422/82.01 |

OTHER PUBLICATIONS

Armour, et al., "Application of chronic intravascular blood glucose sensor in dogs," *Diabetes*, 39:1519-1526, 1990.

(Continued)

*Primary Examiner*—Robert L. Nasser
*Assistant Examiner*—Karen E Toth
(74) *Attorney, Agent, or Firm*—DLA Piper US LLP

(57) ABSTRACT

A tissue-implantable sensor for measurement of solutes in fluids and gases, such as oxygen and glucose, is provided. The sensor includes a multiplicity of detectors, constructed and arranged to improve the probability that one or more detectors will have access to a vascular source at points in time sufficient to permit accurate measurements to be taken. Means and methods for calculating solute levels using the sensor device of the invention are also provided.

25 Claims, 18 Drawing Sheets

OTHER PUBLICATIONS

Bremer, et al., "Benchmark data from the literature for evaluation of new glucose sensing technologies." *Diabetes Technol. Ther.*, 3:409-418 (2001).

Choleau, et al., "Calibration of a subcutaneous amperometric glucose sensor Part 1. Effect of measurement uncertainties on the determination of sensor sensitivity and background current." *Biosens. Bioelectron.*, 17:647-654 (2002).

Choleau, et al., "Calibration of a subcutaneous amperometric glucose sensor implanted for 7 days in diabetic patients Part 2. Superiority of the one-point calibration method." *Biosens. Bioelectron.*, 17:641-646 (2002).

* cited by examiner

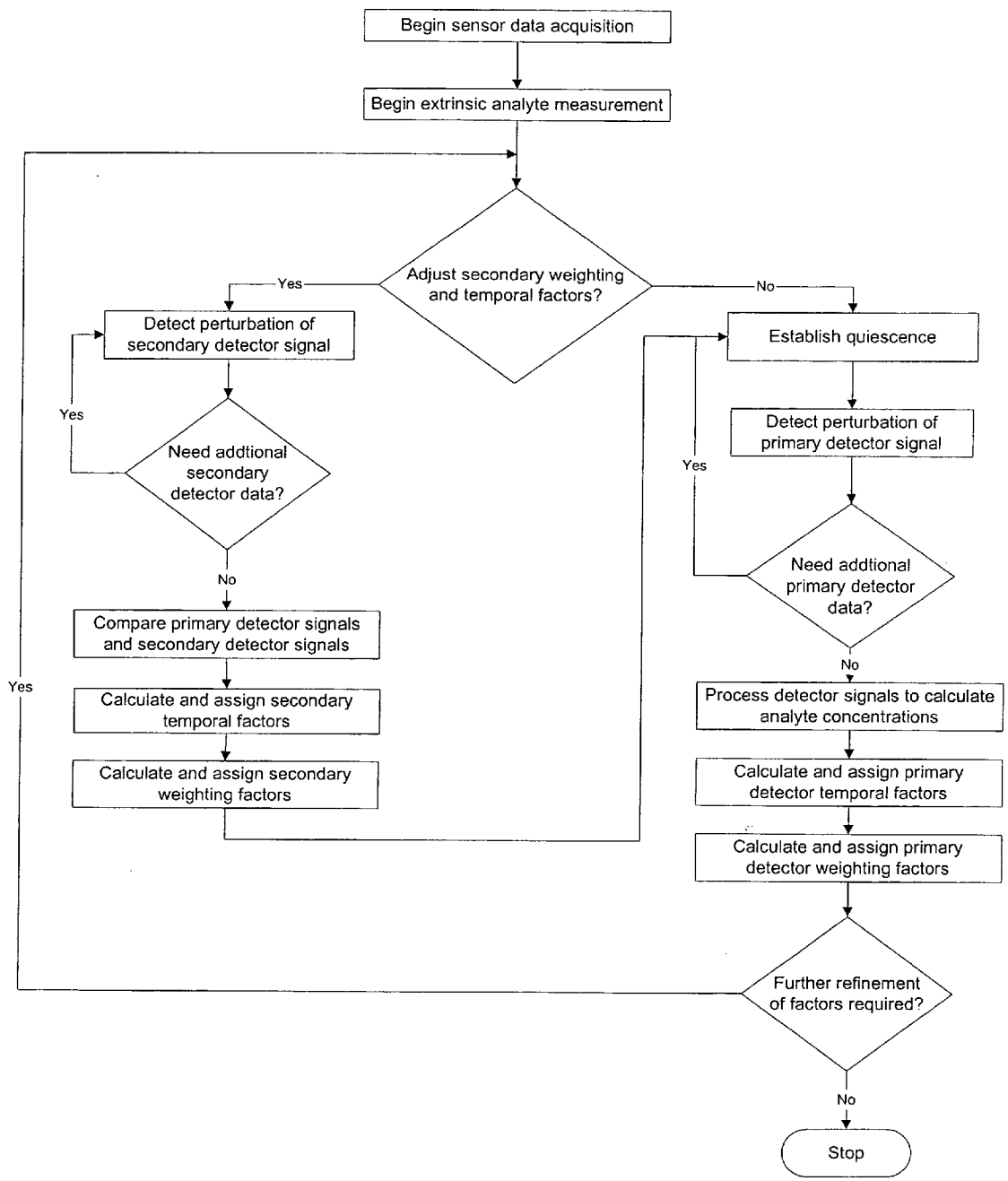
Figure 8 Algorithm for Modifying (or Generating) Signal Adjustment Factors Using Extrinsic Measurements Figure 9 Algorithm for Modifiying Secondary Weighting and Temporal Factors without Extrinsic Measurements
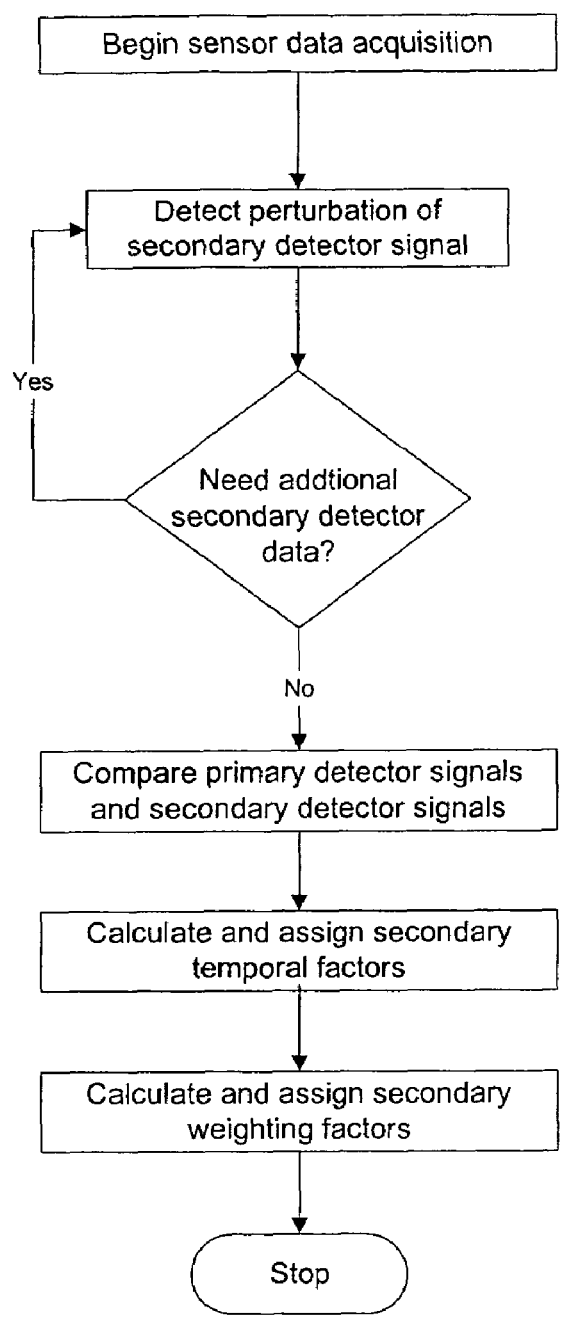

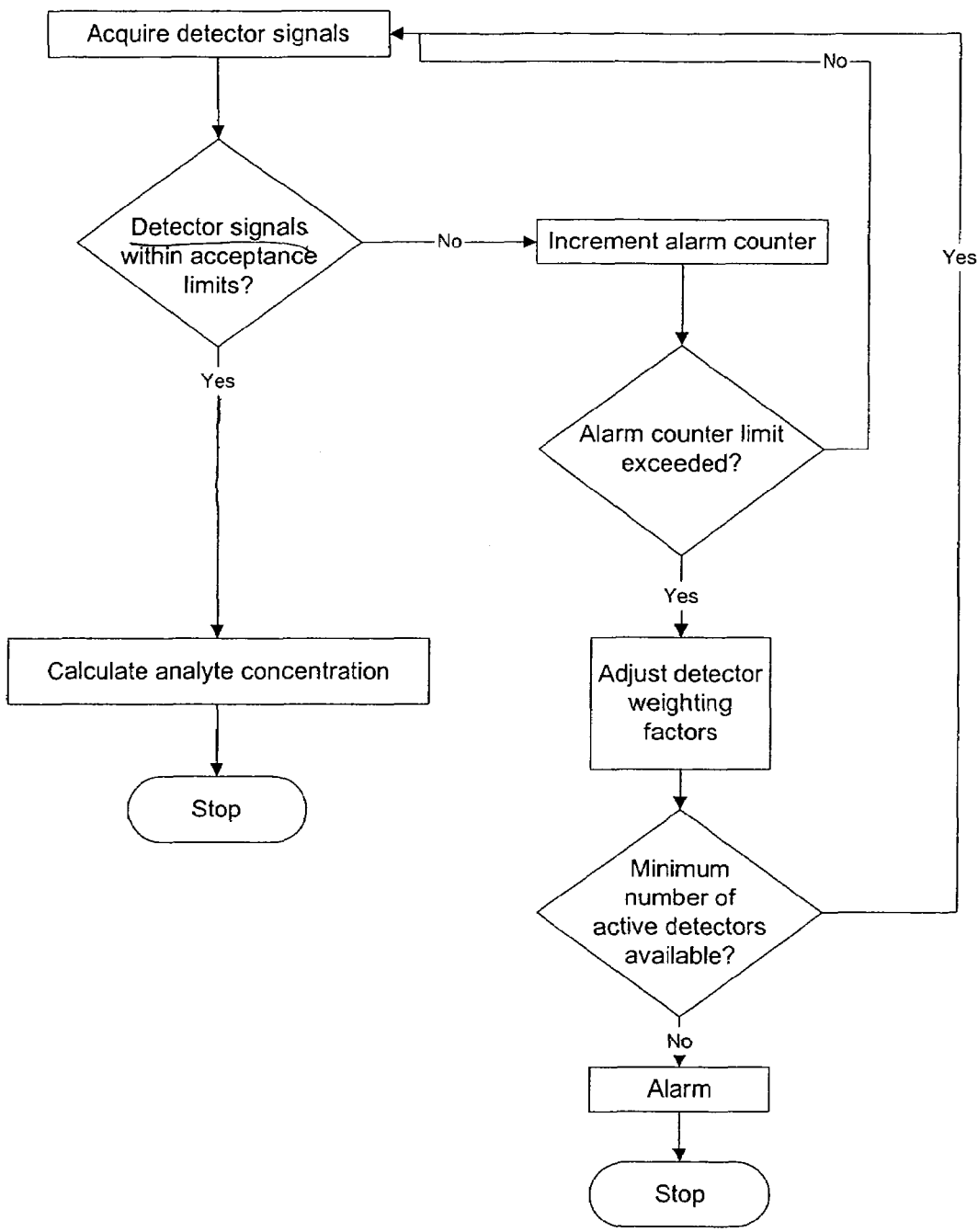
Figure 10 Algorithm for Checking Detector Signal Integrity and Calculating Analyte Concentration

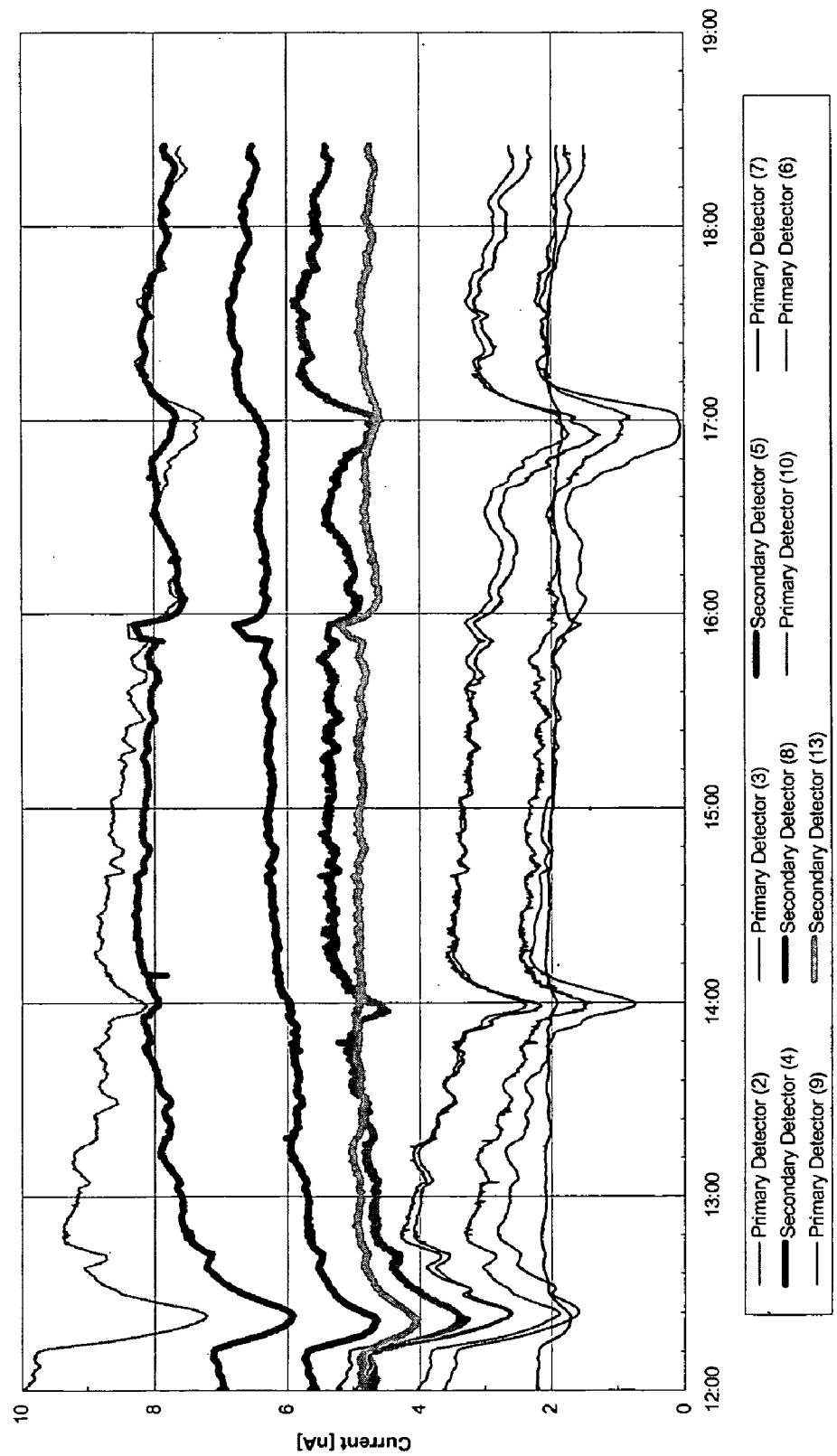

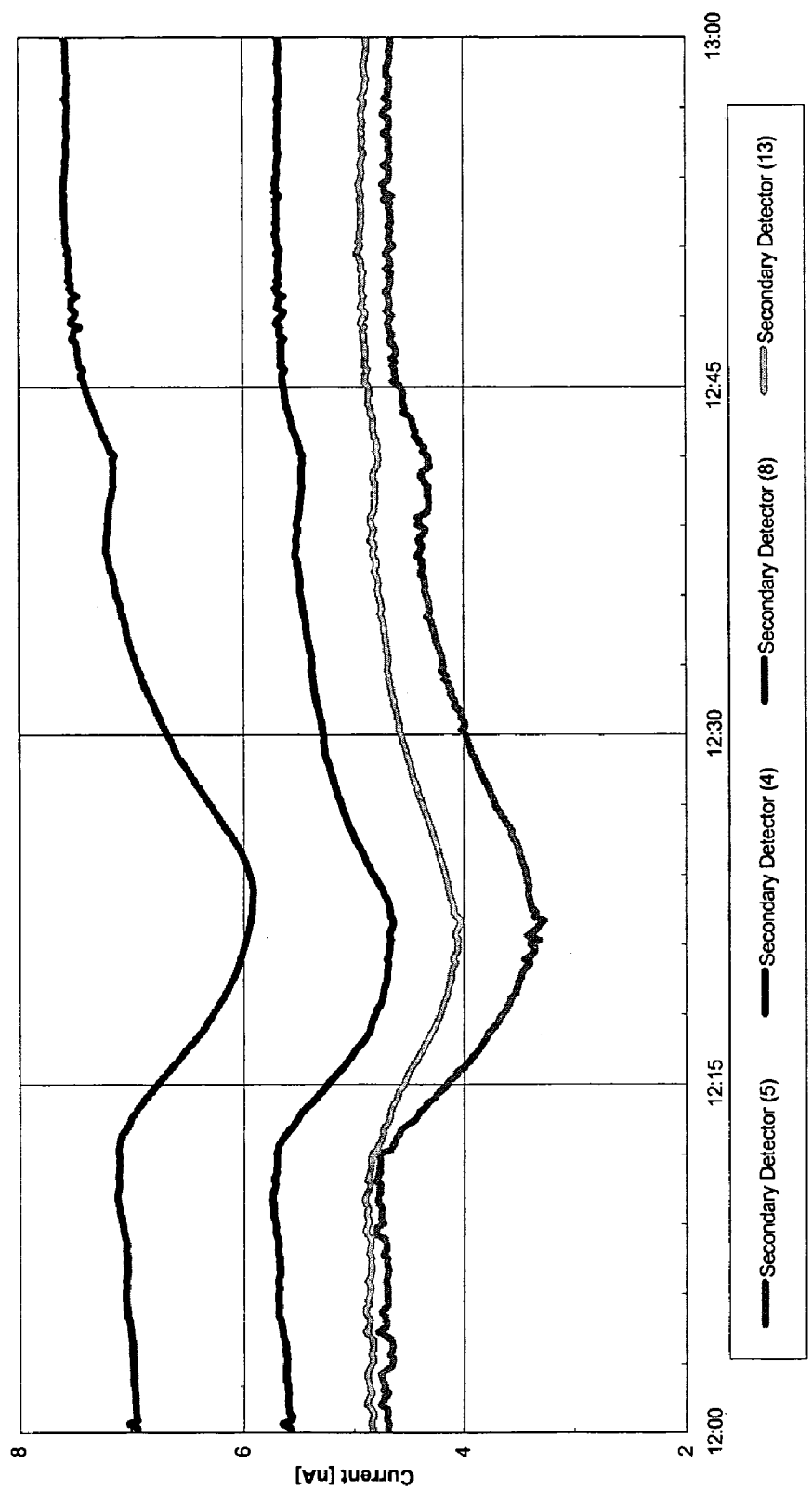

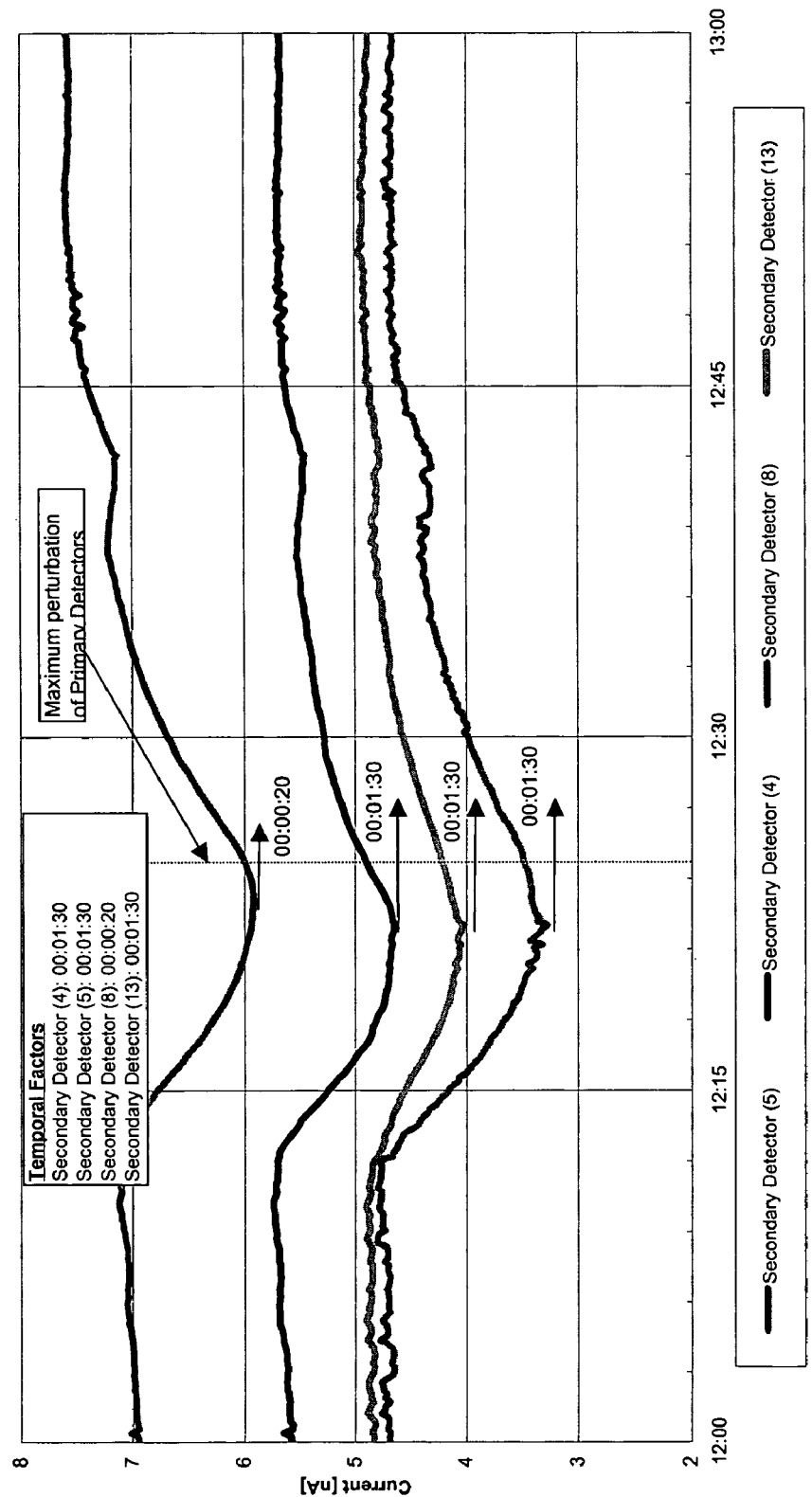

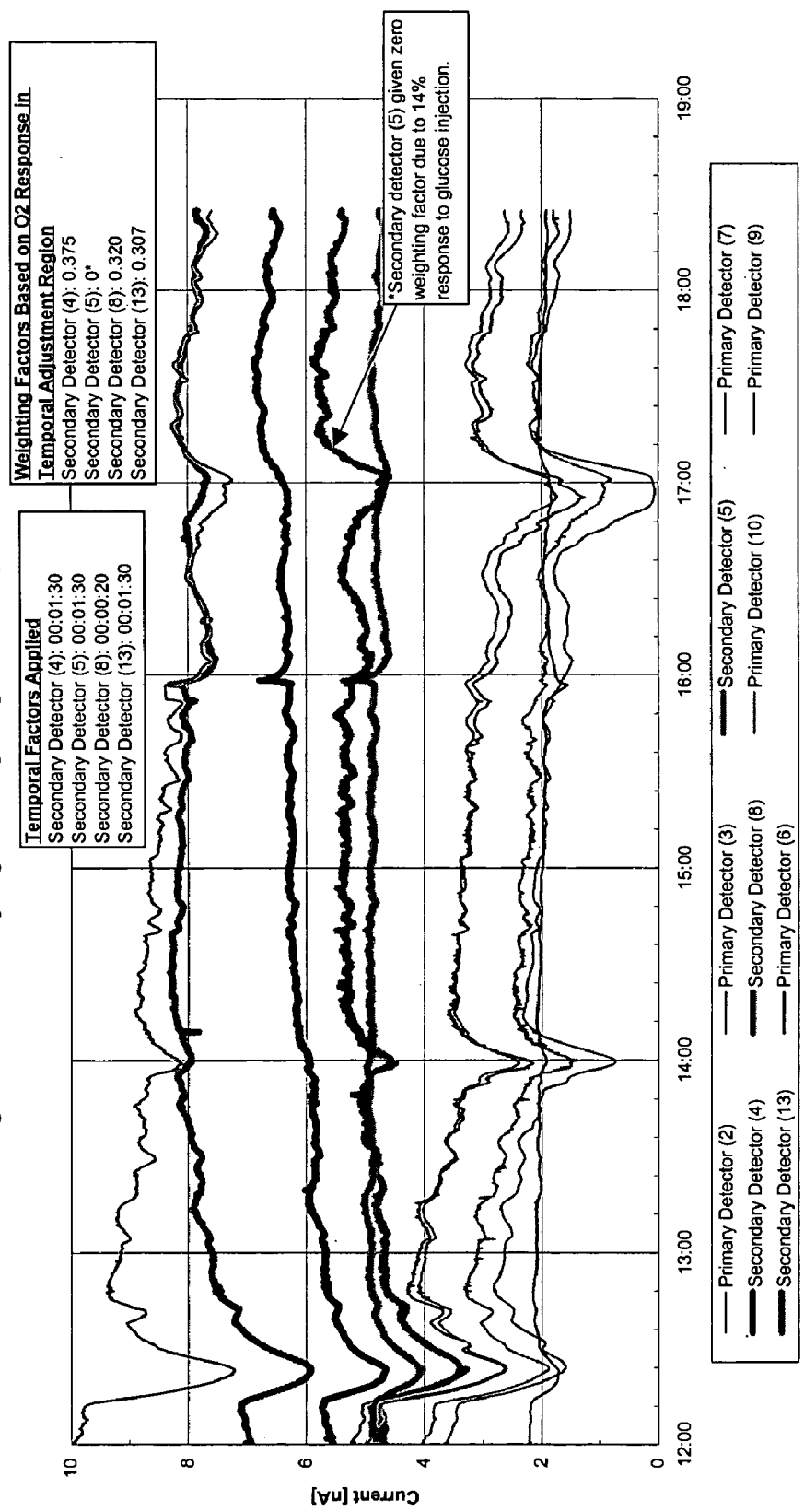

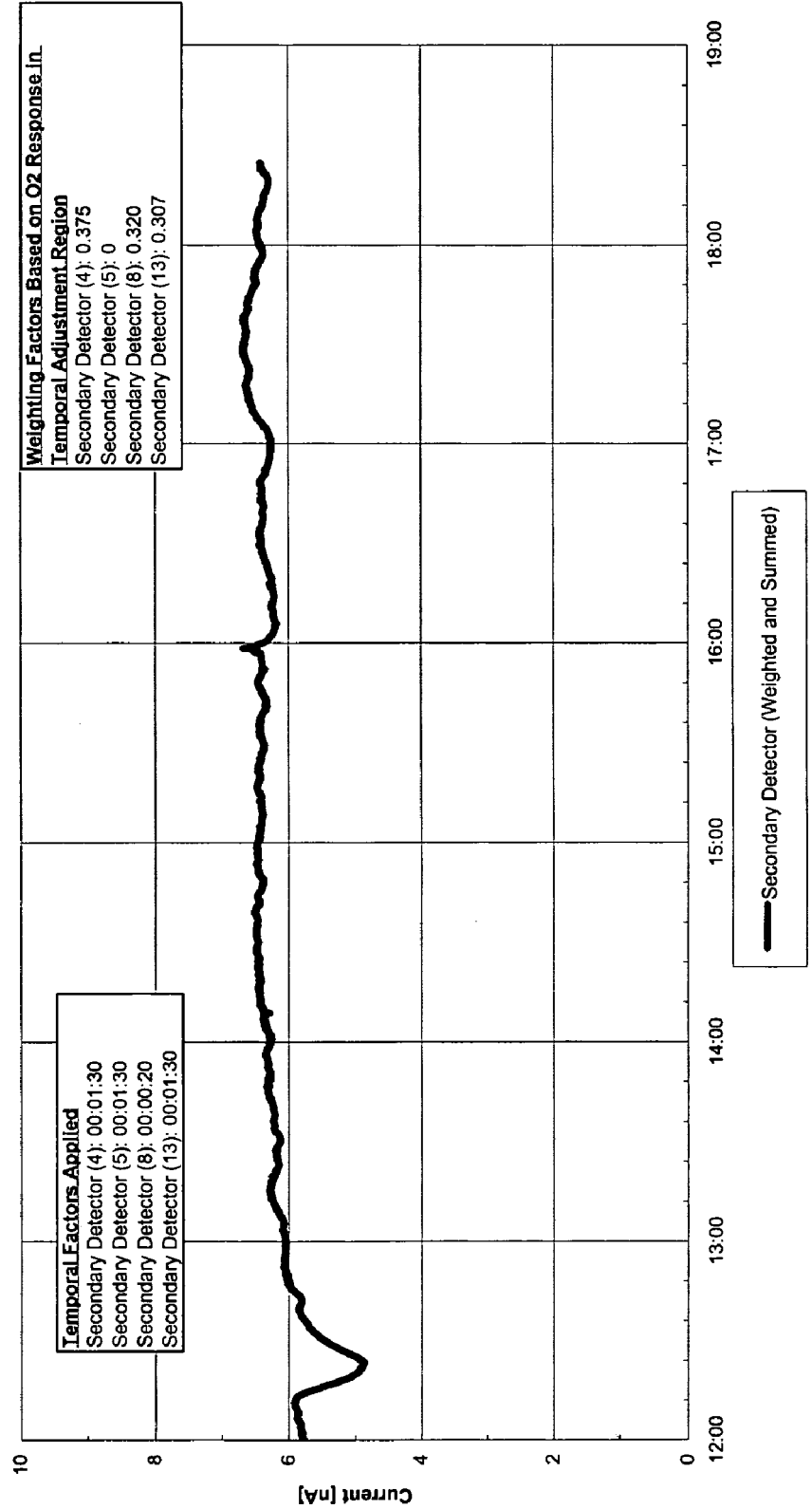
Figure 15: Weighted and Summed Secondary Detector Signal

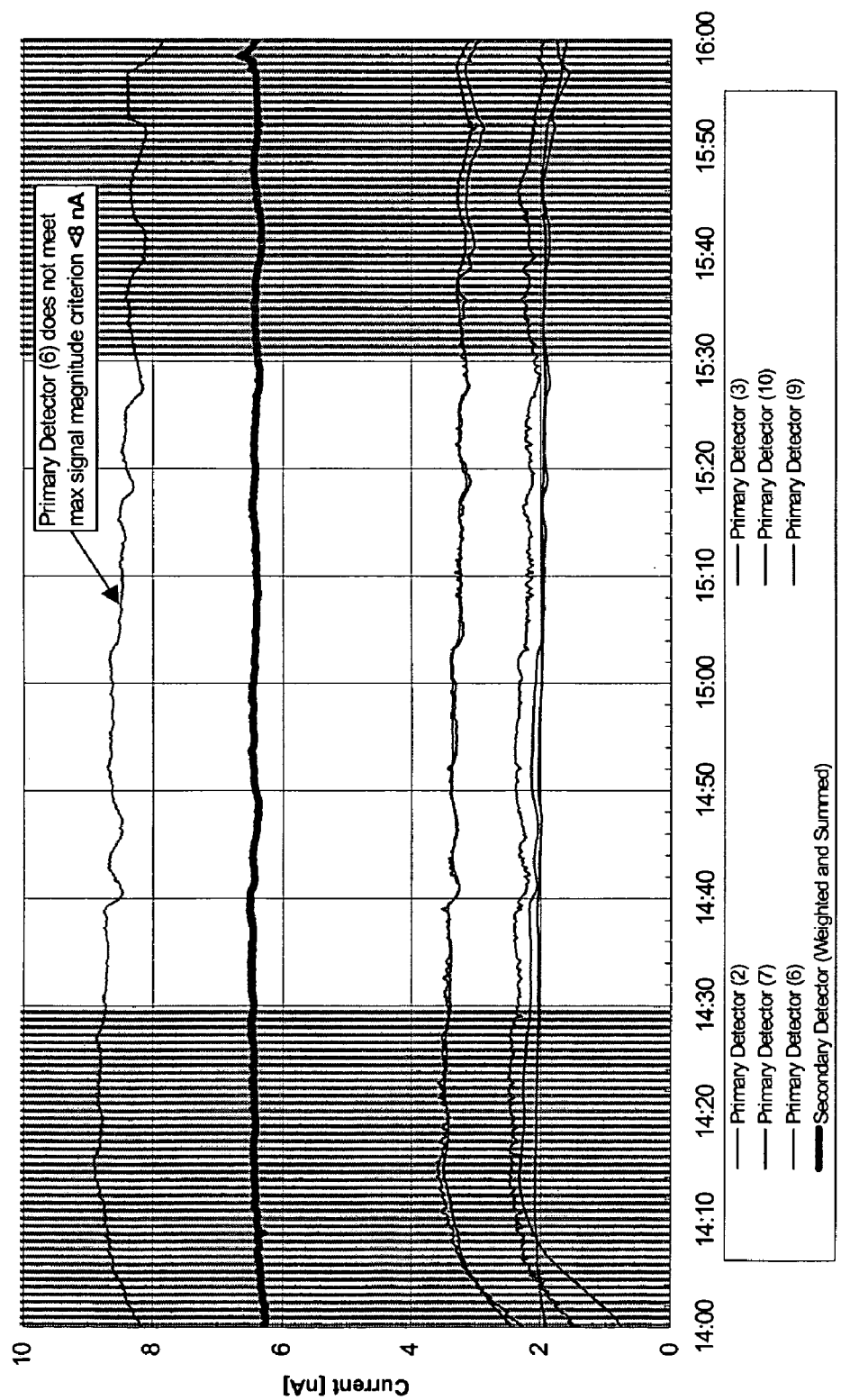

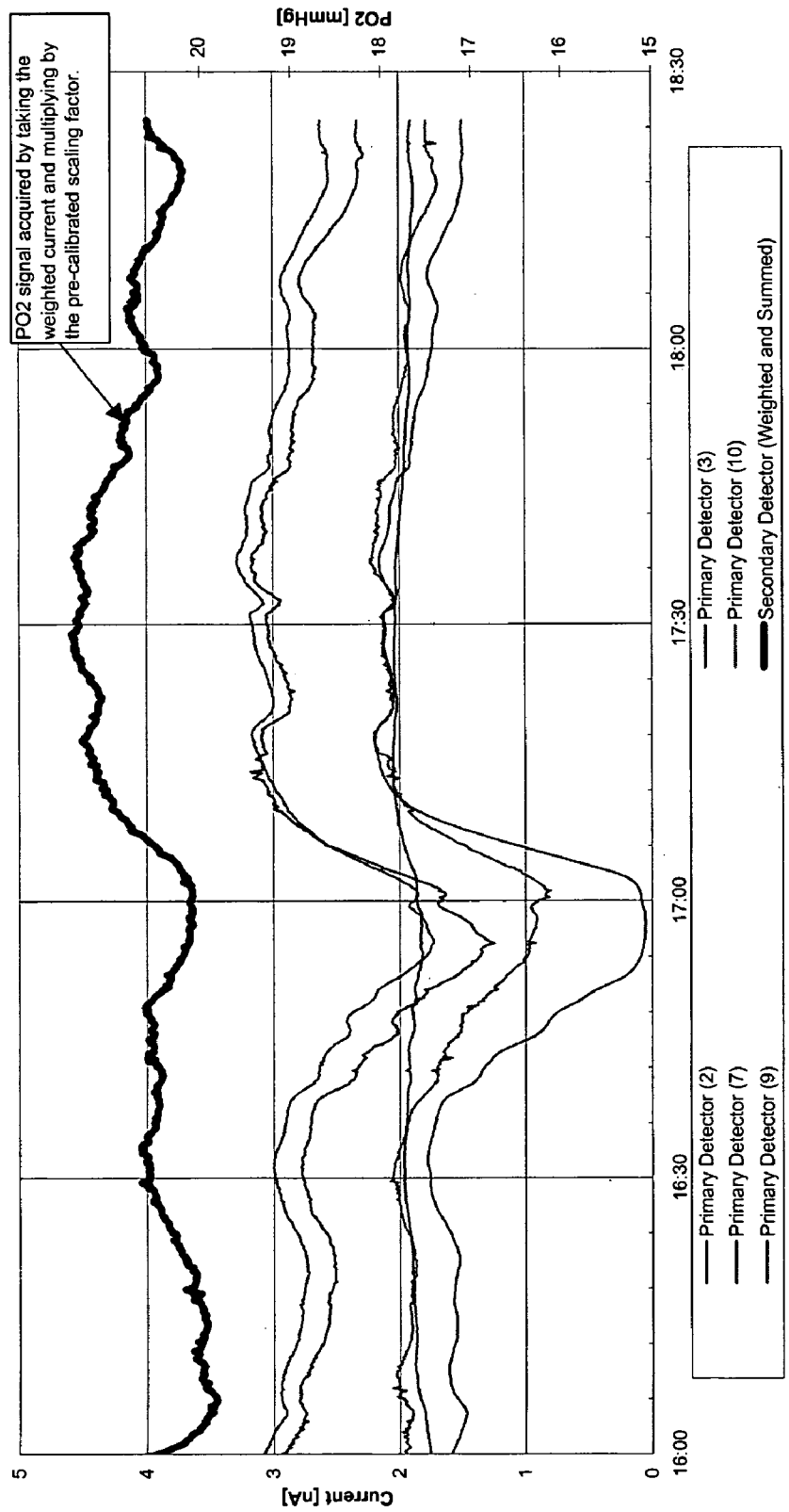
Figure 17: Temporally Adjusted, Weighted and Summed Secondary Signal Converted to PO2 and Raw Primary Signals

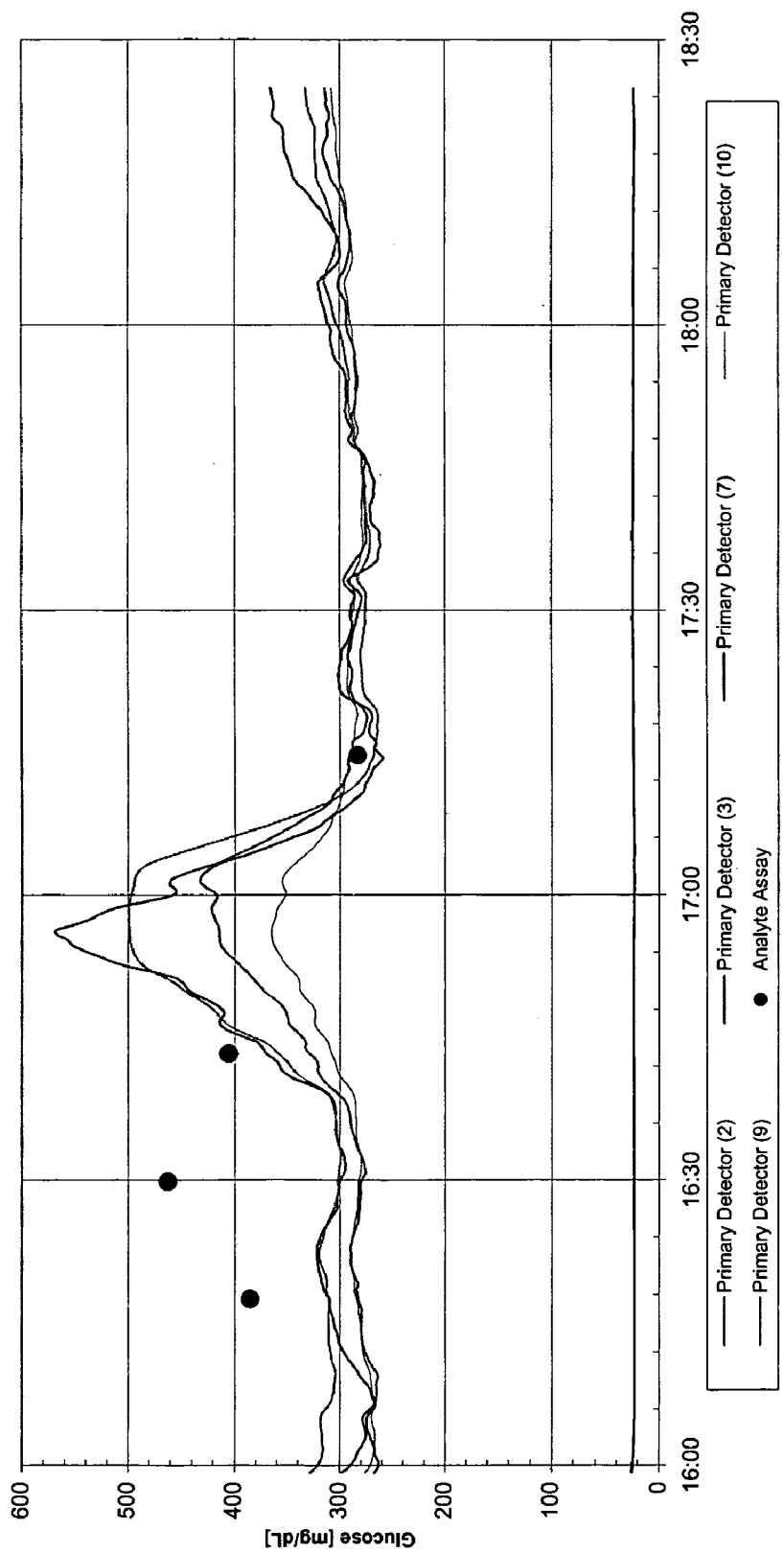
Figure 18: Calculated Analyte Concentrations

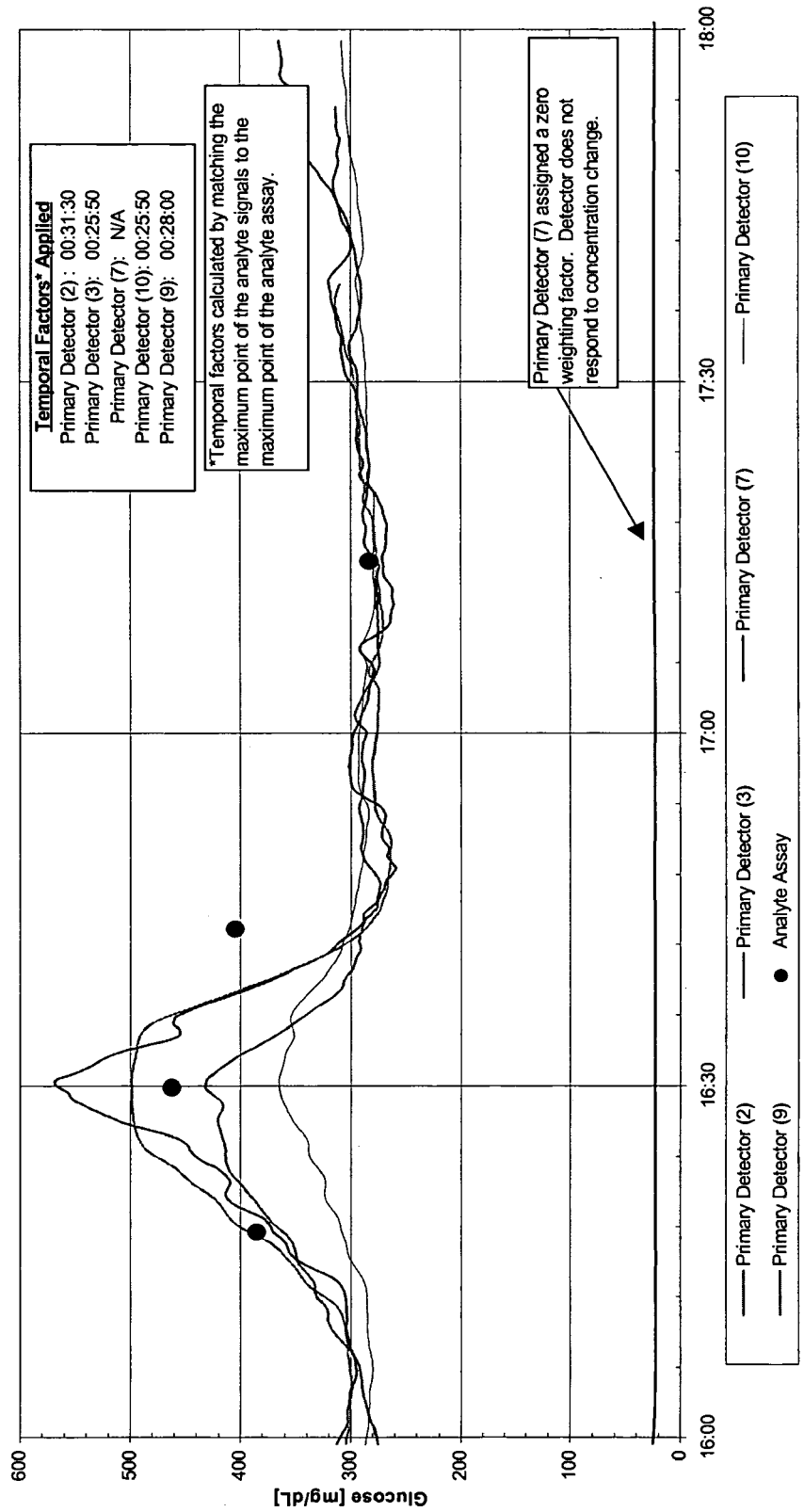

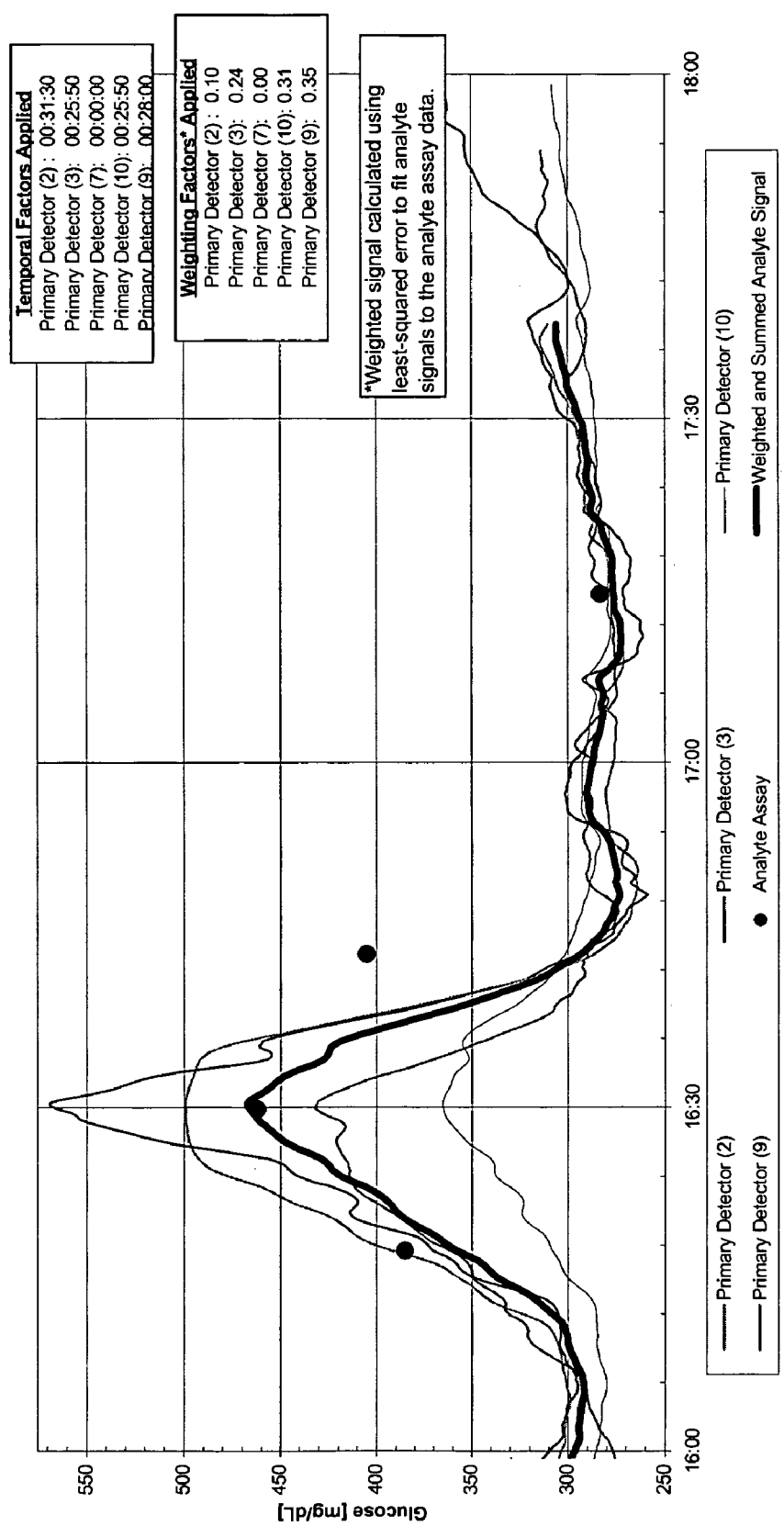

TISSUE IMPLANTABLE SENSORS FOR MEASUREMENT OF BLOOD SOLUTES

This application claims benefit of Provisional application No. 60/423,220 filed Oct. 31, 2002.

BACKGROUND OF THE INVENTION

Regulation of blood glucose is impaired in diabetes by the inability of the pancreas to adequately produce the glucose-regulating hormone insulin and by the insensitivity of various tissues that use insulin to take up glucose. To correct this disregulation requires blood glucose monitoring.

Currently, glucose monitoring in the diabetic population is based largely on collecting blood by "fingersticking" and determining its glucose concentration by conventional assay. This procedure has several disadvantages, including: (1) the discomfort associated with fingersticking, which should be performed repeatedly each day; (2) the near impossibility of sufficiently frequent sampling (some blood glucose excursions require sampling every 20 minutes, or less, to accurately treat); and (3) the requirement that the user initiate blood collection, which precludes warning strategies that rely on automatic early detection. Using the present procedure, the frequent sampling regimen that would be most medically beneficial cannot be realistically expected of even the most committed patients, and automatic sampling, which would be especially useful during periods of sleep, is not available.

Implantable glucose sensors have long been considered as an alternative to intermittent monitoring of blood glucose levels by the fingerstick method of sample collection. The operability of one such sensor has been demonstrated as a central venous implant in dogs (Armour, et al., *Diabetes*, 39:1519–1526 (1990). Although this sensor provided a continuous recording of blood glucose, which is most advantageous for clinical applications, implantation at a central venous site poses risks of blood clot formation and vascular wall damage. The alternative is to implant the sensor in a solid tissue site and to relate the resulting signal to blood glucose concentration.

Typical sensors implanted in solid tissue sites measure the concentration of polar solutes; such as glucose, in the blood perfusing the microcirculation in the vicinity of the sensor. Glucose diffuses from nearby capillaries to the sensor surface. Because such diffusion occurs effectively only over very small distances, the sensor responds to the substrate supply only from nearby blood vessels. Conversely, solutes that are generated in the locality of the sensor may be transported away from the sensor's immediate vicinity by the local microvasculature. In either case, the local microcirculation may influence the sensor's response.

One problem that has confronted previous attempts to implant sensors in solid tissue is that the pattern of blood vessels in the vicinity of the sensor may be highly variable, and may change with time in response to the implantation procedure and the presence of an implant. In some cases, microscopic blood vessels may be close to the sensing element, resulting in substantial diffusive flux and clear, strong signals. In other cases, blood vessels are more distant and sensors appear not to function, to function weakly, or to function only with substantial delays.

Further complicating the spatial inhomogeneity of the microvasculature are the phenomena of vasomotion and variations in regional blood flow. Vasomotion describes the unsynchronized stop-start blood flow cycles that are observed in individual capillaries in living tissue. This phenomenon is characterized by spatial asynchrony—some capillaries have flow while immediate neighbors do not. Vasomotion does not occur continuously or frequently and may be most common when the tissue is otherwise at rest. But, when it occurs, the frequency is about 2 to 4 cycles per minute, with flow interruption in individual capillaries ranging from partial to complete.

Regional blood flow is also affected by posture and the position of the body, such-that localized surface pressure on a blood vessel may occlude it completely, albeit temporarily. The occurrence of such complete occlusion is, of course, not predictable.

Although using biocompatible materials can minimize the tissue response to the implant, capillary distributions or diffusion resistances may still be affected, altering the diffusive flux to the sensor. As such, there is a compelling need for a sensor designed to accommodate the variability of the microvascular structure of solid tissue.

SUMMARY OF THE INVENTION

The invention provides sensors for in vivo detection and measurement of the levels of blood solutes. The sensor is well suited to implantation in solid and gel-like tissues, and is designed to permit long-term monitoring of fluid or gas solute levels on a continuous or near-continuous basis, notwithstanding variations in the structure or condition of the tissue microvasculature.

In particular, the sensor includes a plurality of detectors, each of which is adapted to detect the presence in the tissue of either a specific solute (the "analyte"), such as glucose, or a secondary solute (e.g., oxygen) or confounding phenomenon (e.g., changes in local blood flow). The invention also provides signal processing methods and means incorporating algorithms for calibrating and adjusting data obtained from the sensor for use in mathematically estimating the analyte concentration in the biological environment of interest (e.g., vascularized tissue).

Systematically combining and adjusting data obtained from multiple detectors. (primary, secondary or both) in a sensor according to preselected and calibrated signal adjustment coefficients compensates for inaccuracies in measurements caused by point-to-point variations in analyte concentration and in the magnitude of confounding phenomena, as well as variations over time in same. Such variations may result from variations in tissue vascularization (either within the same tissue over time, or between biological microenvironments in a given tissue at a given time, or between implantation sites); changes in local or regional blood flow at the implantation site; variations in microvascular activity or vasomotion, or formation of fibrous tissue over portions of the implanted sensor. The method of systematically combining and adjusting signals of the present invention also provides a system for ameliorating effects of intrinsic detector drift and failure.

Thus, in general, the invention provides 1) a sensor with multiple detectors (primary, secondary or both); 2) means for adjusting the detector signals by applying signal adjustment coefficients to compensate for phenomena including detector failure, drift, temporal delays, variations between biological microenvironments and confounding phenomena (as defined herein); 3) means for estimating the analyte concentration through use of mathematical calculations based on the detector signals (primary, secondary or both), which may be weighted or summed, to determine a primary composite signal indicative of the concentration of analyte in the biological environment; and 4) means for periodic calibration of the signal adjustment coefficients in order to improve the results of the estimation means.

BRIEF DESCRIPTION OF THE DRAWINGS

FIG. 8 depicts an exemplary signal processing algorithm wherein signal adjustment factors are modified or generated to improve accuracy of analyte concentration calculation. The algorithm incorporates extrinsic measurements of the analyte concentration, and assumes that secondary detectors are part of the sensor.

FIG. 9 depicts an exemplary signal processing algorithm wherein secondary weighting and temporal factors are modified or generated, without any extrinsic measurement of analyte concentration, in order to improve accuracy of analyte concentration calculation.

FIG. 10 depicts an exemplary signal processing algorithm wherein detector signals are checked for rationality before estimation of the analyte concentration.

FIG. 11 shows unprocessed signals from a glucose sensor that uses oxygen detectors and the glucose oxidase-catalyzed depletion of oxygen to measure glucose, the sensor being made according to the invention. The perturbation at about 12:25 in each of the primary signals is approximately simultaneous with the others, but not simultaneous with the secondary signals. Thus, the primary detectors appear to be responding approximately in synchrony with each other.

FIG. 12 shows an enlarged graphical representation of the secondary signals detected during a time period where a perturbation has been detected in both the primary and secondary detectors due to a change in concentration of the coreactant.

FIG. 13 illustrates application of a temporal factor; i.e., the amount of time that each secondary signal is to be delayed in order to coincide with the primary signals.

FIG. 14 illustrates application of weighting factors, wherein the weighting factors applied are directly proportional to each secondary signal's ratio of perturbation amplitude to average signal. Since, in this example, the primary signals appear to be in synchrony with each other, they cannot be individually coupled with a given secondary detector on the basis of sharing a common mode with it. Thus; in this example, the secondary signals can be summed into a single weighted-average time history for the subsequent computation of analyte concentration.

FIG. 15 shows the weighted and summed secondary signals obtained following the application of temporal and weighting factors shown in FIGS. 13 and 14.

FIG. 16 illustrates a period of quiescence for all the detectors, and the observation that primary detector 6 has a signal magnitude that is unacceptable because it exceeds a particular limit, 8 nanoamps in this case, for an extended period.

FIG. 17 shows an enlarged view of the temporally adjusted, weighted-and-summed secondary signals that have been previously calibrated to yield oxygen partial pressure. Also shown are the primary signals obtained over the same time,period.

FIG. 18 illustrates the calculated values of analyte concentration derived from the difference between each primary signal and the weighted-and-summed secondary signals, as well as values for extrinsically measured glucose concentration.

FIG. 19 illustrates the temporal adjustment of the calculated analyte concentrations that has been completed in order to coincide with the extrinsically measured glucose concentration.

FIG. 20 shows the weighted-and-summed calculated analyte concentrations of FIG. 19 superimposed on the individual temporally adjusted calculated analyte concentrations and the extrinsically measured glucose concentration. The values are adjusted to reflect the fact that, because the analyte concentration determined from primary detector 7 does not appear to respond to concentration changes, the detector signal is assigned a primary weighting factor of zero.

DEFINITIONS

Figure 1:
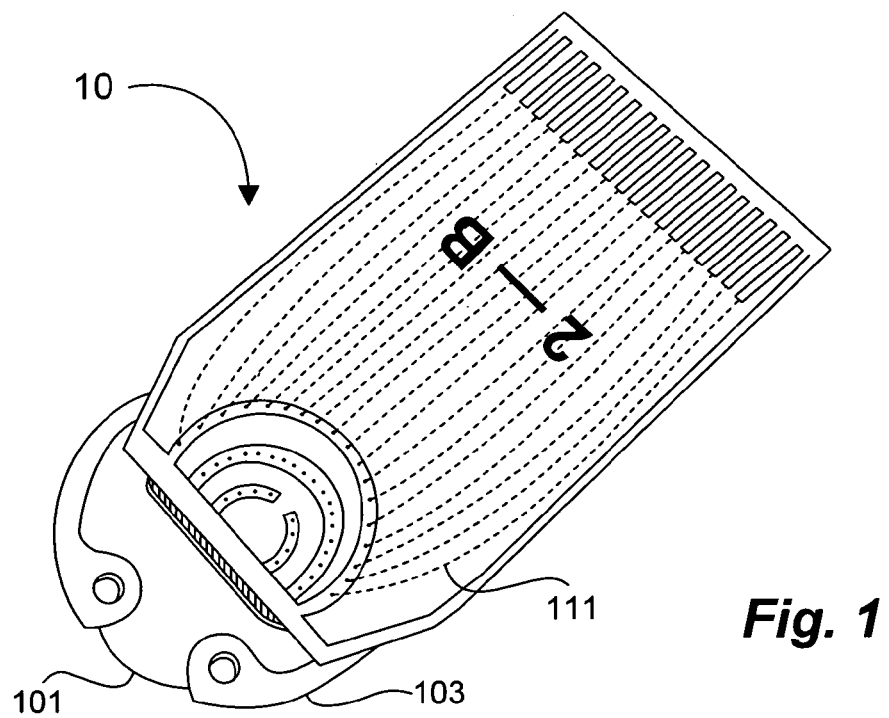
FIG. 1 is a bottom view of a sensor of the invention having a detector platform in the form of a 12.0-mm-diameter disc, and a rectangular connector plate secured to the detector platform. A spring clip is included to secure the assembled detector platform and connector plate to a device used in experimental applications. Wires connecting the detector platform to the connector plate are visible on the surface of the sensor.

The following definitions are provided solely for the purpose of aiding in understanding of the description of the invention to follow. The definitions are not intended to supplant the ordinary meaning or understanding among ordinarily skilled artisans of the terms employed.

Analyte: the solute for which measurement of the concentration and dynamic variation are desired.

Biological Environment: that volume of biological material in communication with a sensor, whose concentration of analyte is capable of being measured by the sensor.

Biological Microenvironment: that volume of biological material in the immediate vicinity of a detector, inside of which the concentration of a given analyte or the magnitude of a given confounding phenomenon is capable of being measured by the detector. The biological microenvironment is typically significantly smaller than, but may be as large as, the biological environment, depending on the analyte or confounding phenomenon being measured by the detector.

Confounding Phenomena: these include physiological attributes whose variation may affect a primary detector's response to the analyte, including rate of perfusion of local and regional vasculature; heart rate, breathing rate, and muscular and physical activity level; local, regional and core temperature; as well as the presence of coreactants and certain chemicals, physiological or otherwise, other than the analyte; e.g., oxygen.

Coreactant: a chemical that is not the analyte, but that is consumed or produced by a reaction that is used in the detection of the analyte.

Detector Area: that area on the surface of a detector through which the detector communicates with its biological microenvironment. The detector area may be non-circular.

Detector Array: a plurality of detectors disposed on a common platform, or that function as a group. The detector array includes at least one primary detector, and may further comprise one or more secondary detectors. Preferably, the detector includes a plurality of primary detectors and at least one secondary detector, or at least one primary detector and a plurality of secondary detectors.

Detector Signal: the information that is derived either directly or indirectly from a detector, wherein such information is indicative of the detector's response to the analyte (in the case of a primary detector) or to the confounding phenomenon (in the case of a secondary detector). Depending on the particular physical principles utilized in the detector, a detector signal may be produced through the action of intervening electronic, optical, mechanical, or chemical apparatus, operatively coupled to the detector. In the invention, detector signals are utilized by signal processing means to produce an estimate of analyte concentration, and may be scaled, normalized, linearized, etc. as appropriate for a given detector's operating principles and individual calibration.

Equivalent Detector Radius: the value that is calculated by dividing the detector area by pi, then taking the square root of the result.

Means for Adjusting Detector Signals: an algorithm and mechanism for its execution (e.g., a software program and microprocessor) for mathematically applying signal adjustment coefficients to detector signals to compensate for detector drift, detector failure, variations between biological microenvironments, and confounding phenomena identified by secondary detectors, if any. Such algorithms may employ parameters including temporal factors, weighting factors, or both.

Means for Calibrating Signal Adjustment Coefficients: an algorithm and a mechanism for its execution (e.g., a software program and microprocessor) that can be employed to adjust signal adjustment coefficients in order to improve the accuracy of the results of the means for estimating analyte concentration.

Means for Estimating Analyte Concentration: an algorithm and a mechanism for its execution (e.g., a software program and microprocessor) that employs at least one predetermined mathematical formula to calculate a value indicative of the analyte concentration in an individual primary detector's biological microenvironment. In sensors which incorporate secondary detectors, such means may utilize secondary detector signals in the calculation.

Primary Composite Signal: data produced from a mathematical combination of estimated analyte concentration from each biological microenvironment. The primary composite signal is indicative of the analyte concentration in the biological environment.

Primary Detector: a device that generates, or can be made to generate, a signal dependent on the concentration of the analyte. Such a device may be based on electrochemical, electrical, optical, mechanical, thermal, or other principles. Such a device may consist of one or more components—such as one, two or three electrodes—and may incorporate immobilized enzymes or other biological or physical components, such as membranes, to provide or enhance sensitivity or specificity for the analyte.

Secondary Composite Signal: data produced from adjusting secondary detector signals, employing means for adjusting, which signals may have been summed. Secondary composite signals may be used in conjunction with primary detector signals in order to estimate analyte concentration.

Secondary Detector: a device that generates, or can be made to generate, a signal corresponding to confounding phenomena. Such a device may be based on electrochemical, electrical, optical, mechanical, thermal, or other principles. Such a device may consist of one or more components—such as one, two or three electrodes—and may incorporate immobilized enzymes or other biological or physical components, such as membranes, to provide or enhance sensitivity or specificity for the coreactants or confounding phenomena.

Sensor: a device comprising a detector array and other elements—such as a housing, electronic circuitry, and a power source—configured to allow generation of signals from the detectors, such signals to be used to make a determination of analyte concentration in the sensor's biological environment.

Signal Adjustment Coefficients: Temporal Factors and Weighting Factors.

Temporal Factors: parameters of an algorithm that may be used by means for adjusting detector signals to filter, accelerate, or delay the detector signal, or value derived from such signal, to match or correlate with other detectors in an array, or with extrinsic detectors that are not part of the same array. Each detector may have its own temporal factors. For a given detector, a single value or multiple values may be utilized as its temporal factor(s).

Weighting Factors: parameters of an algorithm that may be employed by means for adjusting detector signals to adjust the magnitude of a detector signal, or value derived from such signal. Each detector may have its own weighting factors. For a given detector, a single value or multiple values may constitute its weighting factors.

DETAILED DESCRIPTION OF THE PREFERRED EMBODIMENTS

The invention is a tissue-implantable sensor adapted to obtain multiple measurements of a specific solute in a fluid or gas (the "analyte") using at least two detectors arranged as components of a sensor, each communicating independently with signal processing circuitry. The invention is especially well adapted to obtaining data regarding concentrations of analyte in blood (such as glucose), obtained from the vasculature of the tissue surrounding the implant.

Means for adjusting the data utilize signal adjustment coefficients to compensate for time delays in data acquisition, detector drift or failure, variations between the biological microenvironments of each detector, and confounding phenomena. The adjusted data are utilized in mathematical calculations, by means for estimating analyte concentration, to produce a primary composite signal indicative of the actual concentration of analyte present in the biological environment. Such data may further be employed in a model for prediction of future analyte concentrations, such as the model described in co-pending and commonly owned U.S. patent application Ser. No. 09/517,363, filed Mar. 2, 2000.

Figure 2:
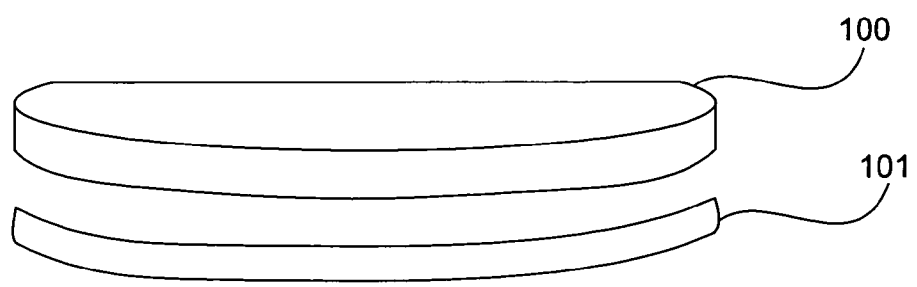
FIG. 2 is an exploded side view of the detector platform and underlying sensor membrane of the sensor of FIG. 1.
Figure 3:
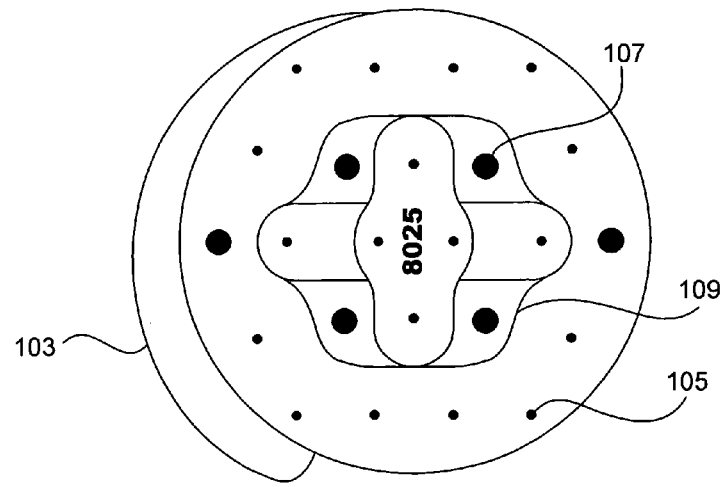
FIG. 3 is a top view of the detector platform of FIG. 1, depicting an array of detectors disposed thereon. Each detector consists of a small (290 μm) diameter disc (working electrode) and a large (875 μm) diameter disc (reference electrode) which work in conjunction with a counter electrode (shown as a sinuous trace in the Figure).

The sensor 10 (FIG. 1) consists of a membrane 101 (FIG. 2) disposed on a detector platform 100 (FIGS. 1, 2 and 3).

Referring to FIG. 3, a multiplicity of detectors (12 are shown) are disposed on detector platform 100 in communication with membrane 101 (shown in FIG. 2). Each detector comprises a working electrode 105, a reference electrode 107, and a counter electrode 109.

Figure 4:
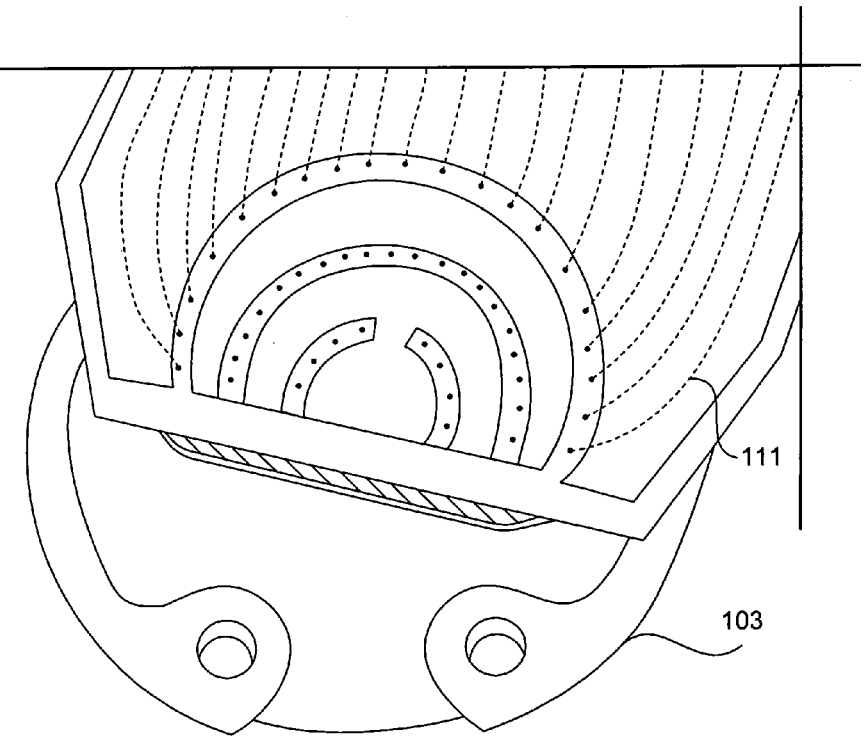
FIG. 4 is a bottom view of the detector platform of FIG. 1 depicting the wire connections between the detector platform and the connector plate.

Means for communicating signals from the sensor to instrumentation comprising signal processing means are also provided. As shown in FIG. 4, the means for communicating signals from the detectors may conventionally be wires, such as wire 111, leading from each individual electrode (e.g., 107) to connection plate 113. Connection plate 113 is secured to detector platform 100. Spring clip 113 is included to secure the assembled connector plate and detector platform to a device used in experimental applications. Connection plate 113 connects to, and communicates with, conventional instrumentation (not shown) employing signal processing means to read, mathematically manipulate (as described further elsewhere below) and display signal data.

Those of ordinary skill in the art will appreciate that alternatives to the particular sensor dimensions, construction and geometry shown in the figures will be suitable for implantation use according to the invention, so long as the basic configuration of primary and, if present, secondary detectors are utilized, and the signal processing means of the invention are employed. Such sensors may be adapted for qualitative and quantitative detection and measurement of any number of different analytes, solutes and confounding phenomena, in addition to those specifically exemplified herein.

In the preferred embodiment where glucose is the blood analyte to be measured (using oxygen detection), the detectors are preferably of the enzyme-electrode type, employing membranes containing immobilized glucose oxidase. Those of ordinary skill in the art will be familiar with the fundamentals of glucose sensor construction, so the materials, methods and alternative forms of construction for such sensors need not be repeated here. By way of example, the following disclosures are incorporated herein by this reference as reflecting non-essential but representative information concerning standard construction techniques for glucose sensors: Gough, U.S, Pat. Nos. 4,484,987; 4,671,288; 4,650,547 and 4,890,620; in Allen, U.S. Pat. No. 5,322,063; in Schulman, U.S. Pat. No. 5,660,163; and in Gough, U.S. Patent Publication No. 20020156355.

Methods for calculating the levels of glucose present as a substrate of a specific enzymatic reaction are well known in the art, as are certain calibration techniques (see, e.g., Choleau, et al., *Biosens. Bioelectron.*, 17:647–654 (2002) and Choleau, et al., *Biosens. Bioelectron.*, 17:641–646 (2002), the teachings of which are incorporated herein by reference). Benchmark data for evaluation of sensor performance are also available (Bremer, et al., *Diabetes Technol. Ther.*, 3:409–418 (2001), the teachings of which are incorporated herein by reference).

For glucose detection, oxygen may be detected and used for indirect measurement of glucose levels, through application of a well-known reaction catalyzed by the enzyme glucose oxidase:

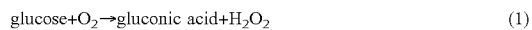

$$\text{glucose} + O_2 \rightarrow \text{gluconic acid} + H_2O_2 \tag{1}$$

The enzyme is immobilized within a matrix that is in contact with an electrochemical oxygen detector. Glucose and ambient oxygen diffuse into the matrix, encounter the enzyme, and the above reaction occurs. The combination of the immobilized enzyme and oxygen-sensitive electrode form a primary detector for glucose, which produces a glucose-modulated oxygen-dependent current, $i_{gmo}$.

Figure 5:
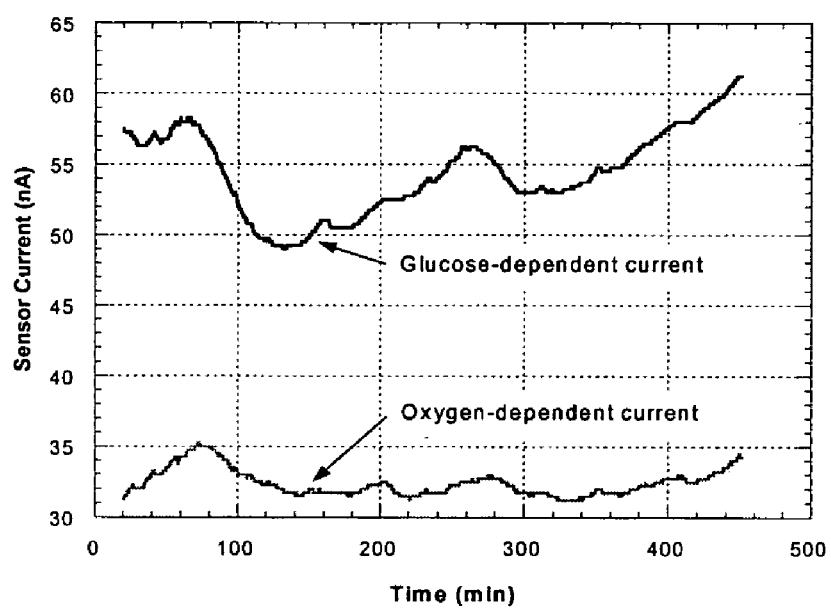
FIG. 5 depicts data typical of current readings obtainable from a dual-detector sensor, consisting of a glucose-sensitive detector and an oxygen-sensitive detector.
Figure 7:
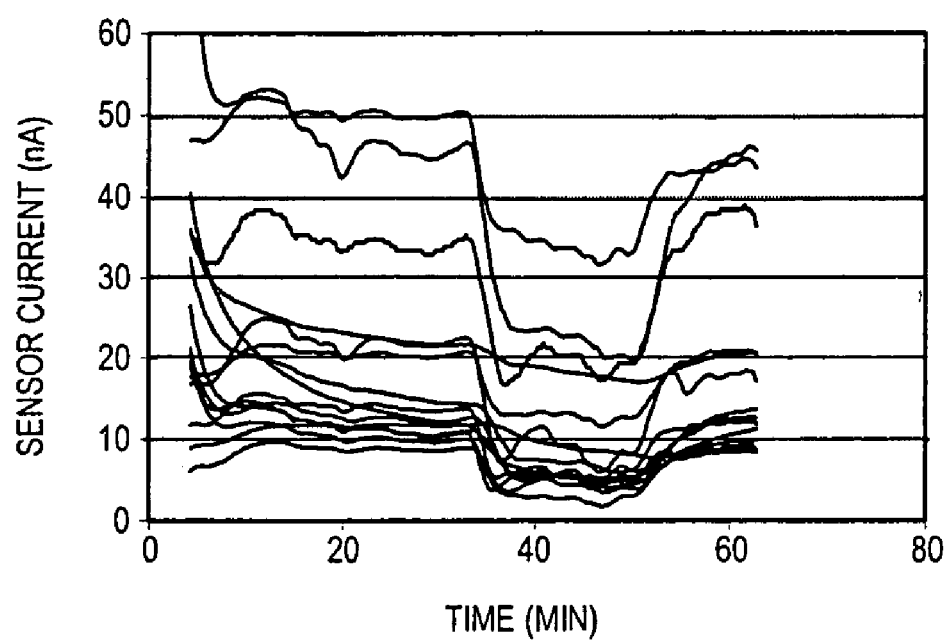
FIG. 7 depicts data obtainable using the sensor described in FIGS. 1–4 to detect alteration of oxygen concentrations in the region of the sensor.

A secondary detector for ambient oxygen, without enzyme, produces an oxygen-dependent current, $i_o$. Excess oxygen not consumed in the enzyme reaction is sensed by the primary detector and, after comparison with the secondary detector, can be related to glucose concentration, using a circuit or software that takes the difference to give the signal of interest, the glucose-dependent difference current, $i_g$. Those of ordinary skill in the art will recognize that other mathematical operations such as scaling of signals could also be advantageously used to produce a signal of interest. Typical readings obtainable from a glucose/oxygen detector-containing sensor are shown in FIG. 5, while readings obtained from the sensor wherein oxygen concentrations varied between the biological microenvironments of the secondary detectors is shown in FIG. 7.

Alternatively, glucose sensors can be constructed to respond to the reaction product hydrogen peroxide. The signal of interest is then the direct detector output. The invention can be applied to either reaction, or to other arrays of chemical detectors designed for implantation.

Whatever the analyte and means for generating a signal responsive thereto, materials utilized in the sensor must be inert, that is they may not release substances that would significantly interfere with the detector operation, and moreover, for implantable sensors, the materials must be biocompatible. Again, those of ordinary skill in the art will be readily familiar with suitable material choices for use in the various elements of the invention such as, for example, the implant-grade alumina utilized in the construction of detector platform 100.

As shown in FIG. 1, detector platform 100 is arranged in a disc configuration. A representative method for fabrication of a sensor using an alumina disc platform is set forth in Example 1; however, the size of the individual electrodes; surface area of the detector platform, and number of detectors present on the platform can vary. In all embodiments of the invention, a multiplicity of detectors, preferably spaced at the minimum distance necessary to ensure their independent operation Without interference from neighbors, are disposed across the sensor surface in an array or other suitable pattern.

Each detector may have a maximum separation from neighbors limited only by the dimensions of the detector platform, and a maximum diameter as dictated by the power supply to, and power consumption by, the sensor. Typically, detectors will be separated by distances up to or exceeding typical capillary separation distances of ~20 to 200 μm.

For use in tissues wherein the detectors will be located at some distance from the capillary, arteriole, and venule sources of blood solutes (either because few such sources are present in the tissue, or because placement of the detector portion of the sensor directly adjacent to a vascular bed cannot be assured), the combined surface area of the detectors may be large compared to the length and width of adjacent vascular bed. The relatively large surface area covered by the multiplicity of detectors increases the probability that one or more detectors will always have reliable access to the tissue microvasculature, notwithstanding changes in the vascular structure and condition. Smaller detectors (in which the combined surface area of the detectors is small compared to the length and width of the vascular source) will be suitable for use where the sensor may be placed adjacent to individual capillaries or arterioles.

The total number of detectors on a sensor is limited only by the surface area of the detector disc, which in turn is dictated by a desire to minimize the overall size of the sensor. In all embodiments of the sensor, use of a multiplicity of detectors: 1) maximizes the probability that several detectors will be positioned very near a vascular bed, 2) affords the possibility of ignoring a given detector if it is or becomes erratic or nonresponsive over time, and 3) minimizes the effects of local variations in analyte concentration, as well as local variations in the magnitude of confounding phenomena.

In some embodiments of the invention, the detector array includes both primary and secondary detectors. Primary detectors are responsive to the analyte, and secondary detectors are responsive to confounding phenomena. In a manner that is dependent on the particular analyte and the detector technology, the primary and secondary sensor signals are combined to produce a measure of the analyte concentration.

In embodiments that utilize both primary and secondary detectors, the detectors may be sized and spaced according to the parameters outlined above. Additionally, it is advantageous in such embodiments to associate (for the purposes of signal processing) a given primary detector with a specific secondary detector (or detectors) whose biological microenvironments have substantially the same magnitude of confounding phenomena.

In this manner, only the most relevant secondary detector signals are used in conjunction with a given primary detector's signal in determining analyte concentration. Such associations may be made a priori, based on geometric proximity of the detectors, or they may be made during calibration or recalibration of the sensor, and determined based on analyses of the detectors' signals. Sample algorithms illustrating techniques for making and utilizing such associations are described elsewhere below.

Use of several different measurement paradigms, collectively or individually, is made possible by the presence of multiple detectors within the sensor. For example, in a glucose sensor, the use of a multiplicity of detectors allows one to combine signals from all detectors to provide a weighted average glucose value. Measurements used to obtain the average value may be taken temporally, i.e., at different points in time, or simultaneously. Values may also be taken spatially, e.g., from detectors at opposite ends of the detector platform. The effect of variations in performance by individual detectors at any given time may therefore be minimized.

Individual detectors may further be provided with geometric dimensions that are large compared to the separation distances of microvessels such that the detectors intrinsically produce spatially averaged signals. In particular, each individual detector may be constructed so as to be likely to contact a multiplicity of capillaries or arterioles, e.g., by ensuring that the width or length of the detector is at least twice the typical capillary separation distances of ~20 to 200 μm.

In a further embodiment of the invention, analyte concentrations are calculated corresponding to each primary detector and subsequently weighted and summed, i.e., a weighted average value is calculated using only signals from those detectors providing a predetermined minimal signal, indicative of proximity to a vascular source. To this end, the most active detectors are identified—using either an extrinsic stimulus, such as an administered glucose challenge, or using only the signals from the detectors—and then, only the signals of the most active detectors are used for analyte concentration measurement. The response of a sensor implanted in an animal subject (hamster) to an administered bolus of glucose is exemplified in FIG. 6. Preferably, the process for identification of minimally active detectors is automated, either by circuitry provided within the implant or by external electronic circuitry activated after the signals from individual detectors are conveyed to an external receiver.

Algorithms for Normalizing Data, Sensor Calibration and Calculation of Analyte Concentration The following algorithms can be used advantageously to process the signals from sensors of the invention that employ more than one primary detector or, for those systems that include secondary detectors, at least one primary detector and more than one secondary detector. These specific algorithms are examples of particular embodiments only. Ordinarily skilled practitioners will recognize that minor modifications of the algorithms described could also be used to practice the invention. All such modifications are considered to be within the scope of the invention.

The first two algorithms described below illustrate useful elements of a calibration means. The third algorithm is an illustrative example of an estimation means.

The following algorithms can be used for electrochemical analyte-sensing systems whose chemistry allows that the analyte concentration can be derived from a single electrochemical reaction, or interrelated set of reactions, as detectable by a single electrode. For example, these algorithms are useful for a glucose-sensing system that uses a detector consisting of an electrode having immobilized glucose oxidase. The glucose oxidase catalyzes a reaction between glucose and oxygen into products, one of which is hydrogen peroxide, the hydrogen peroxide being detectable by the electrode.

A glucose-sensing system that quantifies the depletion of oxygen as glucose reacts with oxygen in the presence of glucose oxidase requires that the ambient oxygen be measured separately. The glucose-modulated oxygen concentration may then be subtracted from the ambient oxygen concentration, the difference being related to glucose concentration.

The algorithms are also useful for electrochemical sensing systems whose chemistry allows or requires the detection of one or more additional, secondary electrochemical reactions to derive or confirm the analyte concentration, or as a means of subtracting the effects of confounding phenomena. For example, the accuracy of the above-described peroxide-based system can be improved by using a secondary detector consisting of an electrode not containing immobilized glucose oxidase, but sensitive to certain interferents present in the biological environment. This secondary detector can be made to generate a signal proportional to the concentration of chemicals that interfere with the quantification of peroxide occurring at the primary detector, such interference including, but not limited to, the production of and drift in a "background" signal. Thus, this secondary signal can be mathematically combined with the signal generated by the primary detector to yield a signal that is more highly correlated to the analyte concentration.

Additional types and numbers of secondary detectors can be accommodated by these algorithms. Such additional secondary detectors can be chemical, optical, electromagnetic, or physical, such as lactate, infra-red, heart rate, or temperature. These detectors can be employed, in addition to the other secondary detectors, to improve the accuracy and reliability of a given analyte-sensing system.

During manufacture, detectors are typically scaled, normalized, linearized, etc. to optimize their accuracy. However, when implanted, several confounding issues arise. Some of these issues are understood, others are not. The result is that some detectors end up providing strong signals, others have weaker or delayed signals, and still others have little or no signal. In order to be useful, these signals may need to be adjusted, and some ignored. Algorithms to accomplish this are described below. For purposes of the following discussion, it should be assumed that the detectors employed have been previously scaled, normalized, linearized, etc. to optimize their accuracy.

The following algorithms use matrices of factors to adjust the individual detector signals, both in magnitude and in time, to optimize the calculation of analyte concentration. In the case of a sensor system that uses only one electrochemical reaction, that is, employs only primary detectors, there are two matrices. These two matrices contain the "primary weighting factors" and the "primary temporal factors." In the case of a sensor system that also uses a secondary detector signal, there are two more matrices. One contains the "secondary weighting factors" and the other contains the "secondary temporal factors." Similarly, additional types of secondary detectors would each require two additional matrices.

The weighting factors multiply the magnitude of their respective detector signals for use in the calculation of analyte concentration. The temporal factors can perform at least two operations on their respective detector signals. They are capable of: (1) delaying select signals by shifting their time domain; and (2) they are capable of filtering and slowing the slew rate of, or damping, select signals. All of these factors can be determined using the algorithms provided herein, or they can be input directly.

The algorithms also identify which signals should be ignored. The criteria used for deciding whether to ignore a given sensor signal include:

1) Absolute magnitude, e.g., does the signal represent an untenably low or high concentration of analyte or magnitude of confounding phenomena?
2) Noise, e.g., does the signal exhibit non-physiologic high frequency fluctuations, or is the signal the only one in the array that fluctuates significantly?
3) Is the signal the only one that does not fluctuate significantly?
4) Does a secondary detector signal fluctuate inappropriately with a change in analyte concentrations?

The algorithms do not prescribe the manner in which a secondary composite signal may be combined with a primary signal to yield a calculation of analyte concentration. Rather, the manner of such calculation is specific to the type of confounding phenomenon measured, as will be well known to those of ordinary skill in the art.

For example, temperature may be measured as a confounding phenomenon and used to correct for its influence on the permeability of a primary detector's overlying membrane to the analyte. The determined temperature may be used advantageously to correct for its known effect by calculating the excursion from a reference temperature and then adjusting the primary detector signal by a fixed percent per degree of excursion. A commonly useful range of such adjustments is three percent to four percent per degree Celsius.

Algorithm for Modifying Signal Adjustment Factors Using Extrinsic Measurements

This algorithm is an example of how one might periodically modify the signal adjustment factors to improve estimation of analyte concentration. If such factors do not already exist, it could also be used to generate them. This particular algorithm requires that at least one extrinsic measurement of the analyte concentration be made and input. In general, greater accuracy would be achieved with the input of greater numbers of extrinsic measurements.

The following are descriptions of the steps involved in this algorithm. The graphical form of this algorithm is shown in FIG. 8.

Begin Sensor Data Acquisition

Start recording the signals from each of the detectors, both primary and secondary as applicable.

Begin Extrinsic Analyte Measurement

With a fingerstick or blood draw, begin to extrinsically determine the analyte concentration. This determination can consist of a single measurement, but preferably includes several.

Adjust Secondary Weighting and Temporal Factors?

It is not necessary to adjust the secondary factors each time the primary factors are adjusted. This is clearly true in the situation where there is no secondary detector, but also in the case where secondary detectors are employed.

Detect Perturbation of Secondary Detector Signal

The perturbation can be spontaneous or induced, but must be of adequate size. The purpose is to identify primary and secondary detector signals that exhibit common modes. Also in this step, detect:

1) Asynchrony between specific primary and secondary detector signals
2) Untenable secondary detector signal magnitudes
3) Noisy secondary signals Need Additional Secondary Detector Data?

In a sensor with an array of detectors, an adequate signal perturbation may occur in only one portion of the array. While this perturbation will be useful for those particular detectors where it occurs, a perturbation should also be sought in each of the detectors whose performance is to be optimized. Further, if more than one type of secondary detector exists, then a perturbation in each of these other secondary detectors must be detected separately from the other secondary detectors. Thus, in general, perturbation detection would be performed repeatedly.

Compare Primary Detector Signals and Secondary Detector Signals

Here the secondary detector signals that share a common mode with a given primary detector signal are identified and "grouped" with it. One may take this opportunity to observe whether any secondary signals fluctuate inappropriately during a perturbation of the primary signal. Such secondary detectors should be ignored, that is, given a weighting factor of zero in the next step of this example.

Calculate and Assign Secondary Temporal Factors

Here, the perturbations are aligned in the time domain by delaying those detector signals, either primary or secondary, that lead the other(s) within each group whose members share a common mode. In addition, the slew rates can be made to approximate one another by choking, or damping, those detector signals that slew more quickly than the other(s) in its group.

Calculate and Assign Secondary Weighting Factors

Those secondary detectors identified above are given weights which, for a given primary detector grouping, may conveniently sum to 1.0. If a given primary detector shares a common mode with only one secondary detector, then that secondary detector's weighting factor is 1.0 in relation to that primary detector. If more than one secondary detector shares a common mode with a given primary detector, then their weights may be based on proximity, signal strength, degree of synchrony, or some combination of these. Those secondary detector signals that are too small or large, noisy, or asynchronous with all primary detectors are assigned a secondary weighting factor of zero.

Establish Quiescence

Wait for a period when the detector signals do not change rapidly. The detector signals, both primary and secondary, that are not changing rapidly during this portion of this algorithm provide a basis for calculating the adjustment factors that are more consistent and accurate than if the signals are changing rapidly.

Detect Perturbation of Primary Detector Signal

Like the secondary signal, this perturbation can be spontaneous or induced. Also detected at this time are primary detector signals that are:
1) Too large or small
2) Too noisy Need Additional Primary Data?

If one or more primary detector signals are unsatisfactory, as identified above, then the detection may be repeated some finite number of times.

After some finite number of failures to detect a satisfactory signal from a given primary detector, that detector's signal may be ignored until the next time that the adjustment algorithm is run.

Process Detector Signals to Calculate Analyte Concentration

Here, the adjusted secondary detector signals that have been grouped with a given primary detector are used to calculate analyte concentration(s).

Calculate and Assign Primary Detector Temporal Factors

The primary detector signals are time-shifted, and possibly damped, to minimize temporal mismatch with the extrinsic analyte measurement.

Calculate Primary Detector Weighting Factors

Each calculated analyte concentration is compared to the extrinsic measurement and adjusted by a weighting factor for the best fit, e.g. least-squares, to the extrinsically determined analyte concentration.

Alternatively, linear combinations of the calculated concentrations may be formulated for the best fit with the extrinsic measurements. In this alternative, best fit primary detector weighting factors should be also be calculated for reduced numbers of available calculated analyte concentrations (one associated typically with each primary detector) in the event that one or more detectors becomes inoperative in the future.

Further Refinement?

All the adjustment factors, in general, may be functions of analyte concentration and of magnitude of confounding phenomena. So the factor adjustment algorithm may be repeated at different such concentrations or magnitudes. However, repetition may prove unnecessary.

Algorithm for Modifying Secondary Weighting and Temporal Factors Without Using Extrinsic Measurements This algorithm is an example of how one might periodically modify the secondary weighting and temporal factors to improve estimation of analyte concentration. If such factors do not already exist, it could also be used to generate them. This particular algorithm requires no extrinsic input.

The following are brief descriptions of the steps involved in this algorithm. The graphical form of this algorithm is shown in FIG. 9.

Begin Sensor Data Acquisition

Start recording the signals from each of the detectors, both primary and secondary as applicable.

Detect Perturbation of Secondary Detector Signal

The perturbation can be spontaneous or induced, but must be of adequate size. The purpose is to identify primary and secondary detector signals that exhibit common modes. Also in this step, detect:
1) Asynchrony between specific primary and secondary detector signals
2) Untenable secondary detector signal magnitudes
3) Noisy secondary detector signals Need Additional Secondary Detector Data?

In a sensor with an array of detectors, an adequate signal perturbation may occur in only one portion of the array. While this perturbation will be useful for those particular detectors where it occurs, a perturbation should also be sought in each of the detectors whose performance is to be optimized. Further, if more than one type of secondary detector exists, then a perturbation in each of these other secondary detectors must be detected separately from the other secondary detectors. Thus, in general, perturbation detection would be performed repeatedly.

Compare Primary Detector Signals and Secondary Detector Signals

Here the secondary signals that share a common mode with a given primary detector are identified and "grouped" with it.

Calculate and Assign Secondary Temporal Factors

Here, the perturbations are aligned in the time domain by delaying those signals, either primary or secondary, that lead the other(s) within each group whose members share a common mode. In addition, the slew rates are made to approximate one another by choking, or damping, those detector signals that slew more quickly than the other(s) in its group.

Calculate and Assign Secondary Weighting Factors

Those secondary detectors identified above are given weights which, for a given primary detector grouping, may conveniently sum to 1.0. If a given primary detector shares a common mode with only one secondary detector, then that secondary detector's weighting factor is 1.0 in relation to that primary detector. If more than one secondary detector shares a common mode with a given primary detector, then their weights may be based on proximity, signal strength, degree of synchrony, or some combination of these. Those secondary detector signals that are too small or large, noisy, or asynchronous with all primary detectors are assigned a secondary weighting factor of zero.

Algorithm for Checking Detector Signal Integrity and Calculating Analyte Concentration This algorithm is an example of how one might periodically check the detector signals for reasonableness before calculating the analyte concentration. If a signal, or signals, is not reasonable, it is checked again up to some maximum number of times. Then, if it is still unreasonable, it is ignored. Then the analyte concentration is calculated. This particular algorithm requires no extrinsic input.

The following are brief descriptions of the steps involved in this algorithm. The graphical form of this algorithm is shown in FIG. 10.

Acquire Detector Signals

Signals from each of the primary—and secondary, as applicable—detectors are recorded for some time period.

Detector Signals Within Acceptance Limits?

The recorded signals are checked against acceptance criteria:
1) Excessive high-frequency noise, e.g., instability
2) Untenably high or low signal magnitude If any of the signals are unacceptable, then skip the next three commands in this list. Otherwise, proceed sequentially.

Calculate Analyte Concentration

In the case that the analyte-sensing system utilizes secondary detectors, then their signals are first adjusted by their temporal factors. In the case that multiple secondary detectors are grouped with a given primary detector, then those secondary detector signals are adjusted by their weighting factors and summed to form a secondary composite signal. Then the secondary detector signals—or secondary composite signals, as applicable—are mathematically combined with the primary detector signals to create calculated analyte concentrations. The resulting calculated analyte concentrations are adjusted by their temporal factors, and then combined mathematically using their weighting factors to create the primary composite signal which is indicative of the analyte concentration in the biological environment.

Stop

Increment Alarm Counter

An alarm counter, specific to each detector, is incremented to note the number of times that the detector failed to produce an acceptable signal. The alarm counter may have separate limits for failures that occur sequentially and those that occur during separate integrity checks.

Alarm Counter Limit Exceeded?

For a given detector, the value of its alarm counter is compared to its preset limit. If the counter is less than the limit, then one returns to the beginning of the algorithm to acquire additional signals for all the detector. Otherwise, proceed sequentially.

Adjust Detector Weighting Factors

If, for a given detector, the value of its alarm counter is equal to or greater than its preset limit, then weighting factors are adjusted to effectively ignore that detector. If the detector whose alarm counter is too high is a primary detector, then its associated primary weighting factor is set to zero, until the next time that the primary weighting factors are adjusted again. If the detector whose alarm counter is too high is a secondary detector, then its associated secondary weighting factor is set to zero, until the next time that the secondary weighting factors are adjusted again. In this latter case, if there are other secondary detectors in its grouping with a primary detector, then the weighting factors of those other detectors are multiplied by the factor necessary to cause the weighting factors to sum to 1.0. If there is no other secondary detector in its grouping, then the weighting factor, of the associated primary detector is set to zero and the weighting factors of the other primary detector are adjusted accordingly.

Minimum Number of Active Detectors Available?

The number of active detectors remaining is compared to a preset limit. If the number available is greater than or equal to the minimum, then one returns to the beginning of the algorithm to acquire additional, signals for all the detectors. Otherwise, proceed sequentially Alarm An alarm sounds to indicate malfunction.

Stop

The invention having been described, examples illustrating its implementation and practice are provided. These examples do not in any way limit the scope of the invention, which is defined by the appended claims.

EXAMPLE 1

Method for Fabricating a Tissue Implantable Glucose Sensor

1) Using standard thick-film techniques, create conductive vias through an implant-grade alumina disc.
2) Print and fire an electrode array of high-purity platinum onto the disc, aligning the electrodes with their respective conductive vias. These electrodes will become the working, reference and counter electrodes of the detectors.
3) Print and fire insulating dielectric layers, as necessary.
4) Electrochemically apply Ag/AgCl to the reference electrodes.
5) Using wirebonding, or other conventional circuit fabrication techniques, provide connections from the electrodes of the detector array to conventional potentiostat circuitry.
6) Affix a multilayer glucose oxidase-impregnated membrane to the face of the disc. The outer layer of this membrane is silicone rubber; the glucose oxidase is impregnated in a fashion that supplies oxygen in relative excess to the glucose oxidase (see, for example, co-pending and commonly owned U.S. patent application Ser. No. 10/078,567, incorporated herein by reference).

Using the above fabrication method, a sensor as shown in FIGS. 1 through 4 was constructed, having 12 glucose detectors and 6 oxygen detectors.

EXAMPLE 2

Improvement in Stability of Glucose Measurements Using the Sensor of the Invention FIG. 5 depicts data typical of current readings obtainable in vitro from a dual-detector sensor, consisting of a glucose-sensitive detector and an oxygen-sensitive detector.

A sensor constructed as described in Example 1 was implanted in a live, healthy hamster. In particular, two titanium plates, each of which includes a small "window," are placed so as to support a thin layer of retractor muscle beneath excised subcutaneous tissue on the animal's back. A cover glass was placed in the window over one side of the exposed skin, and the sensor device was fixed onto the opposite side. Catheters were placed in the carotid artery and jugular vein for sampling and fluid delivery. The resulting structure is a layer of tissue 100 μm thick by 12 mm in diameter, having intact microvasculature.

Figure 6:
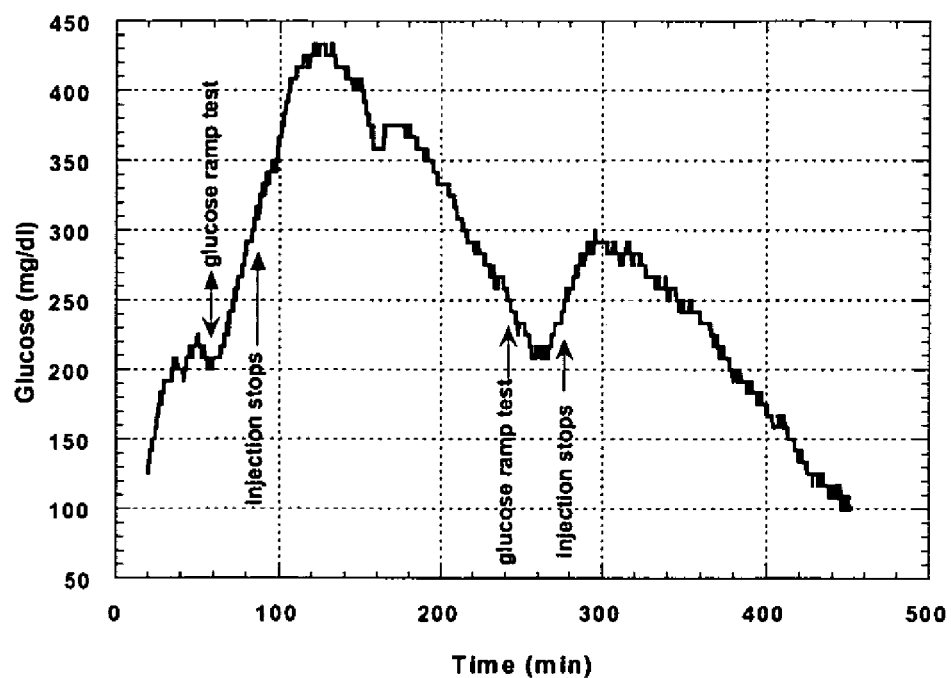
FIG. 6 depicts data obtainable using the sensor described in FIGS. 1–4 on introduction of a bolus of 60 μl/minute of 50 gm % glucose over a minute, followed by infusion of 16 μl/min for 15 minutes.

To provide stimulus to the glucose detector, a bolus of 60 μl/minute of 50 gm % glucose was introduced into the catheterized vessels over a period of a minute, followed by introduction of 16 μl/min of glucose for 15 minutes. The data obtained in response to exposure to a defined quantity of glucose are shown in FIG. 6.

Thirty three, minutes following introduction of the glucose, inspired oxygen was changed from atmospheric levels (20.9%) to 15%, then back to atmospheric at t=50, minutes. Although the detectors possessed nearly equal sensitivities as measured in vitro prior to implantation, the influence of the tissue implantation caused significant variations in performance between individual detectors. These variations demonstrate the need for a sensor containing a multiplicity of detectors made according to the invention to ensure consistent measurements notwithstanding microenvironmental variations affecting tissue-implanted sensors.

EXAMPLE 3

Application of Signal Processing Algorithms

In the following figures, the time course of measurements taken is indicated along the horizontal axis of each graph. Either the measured current or detected analyte concentration is indicated along the vertical axis of each graph, as shown.

FIG. 11 shows unprocessed primary and secondary detector signals from a glucose sensor that uses oxygen detectors and the glucose oxidase-catalyzed depletion of oxygen to measure glucose, the sensor being made according to the invention. The perturbation at about 12:25 in each of the primary detector signals is approximately simultaneous with the others, but not simultaneous with the secondary detector signals. Thus, the primary detectors appear to be responding approximately in synchrony with each other.

FIG. 12 shows an enlarged view of the secondary detector signals during a time period where a perturbation has been detected in the signals of both the primary and secondary detectors due to a change in concentration of the coreactant, oxygen.

FIG. 13 illustrates the amount of time that each secondary detector signal is to be delayed in order to coincide with the primary detector signals.

Since, in this example, the primary detector signals appear to be in synchrony with each other, they cannot be individually coupled with a given secondary detector on the basis of sharing a common mode with its signal. Thus, in this example, the secondary detector signals can be summed into a single weighted-average time history for the subsequent computation of analyte concentration. The weighting factors shown in. FIG. 14 are in direct proportion to each secondary detector signal's ratio of perturbation amplitude to average signal. Also shown in FIG. 13 is that secondary detector 5 is assigned a weighting factor of zero because of its inappropriate response to a fluctuation in analyte concentration, to which it is not otherwise expected to be sensitive.

FIG. 15 shows the weighted and summed secondary detector signals.

FIG. 16 illustrates a period of quiescence for all the detectors, and the observation that primary detector 6 exceeds a maximum continuous output criterion of 8 nano-amps.

FIG. 17 shows an enlarged view of the temporally adjusted, weighted-and-summed secondary detector signals that have been scaled by additional calibration factors to yield oxygen partial pressure. Also shown are the primary detector signals in the same time period.

FIG. 18 illustrates the calculated values of analyte concentration derived from the mathematical combination of each primary detector signal and the weighted-and-summed secondary detector signals, that is, the secondary composite signal. This figure also shows the values of the extrinsically measured glucose concentration.

FIG. 19 illustrates the temporal adjustment of the calculated analyte concentrations that has been completed in order to coincide with the extrinsically measured glucose concentration. Since the analyte concentration that was calculated from primary detector 7 does not appear to respond to concentration changes, it is assigned a primary weighting factor of zero, refer to FIG. 20. In this example, primary detector signals are seen to lag the extrinsically measured glucose concentration by significant durations, the greatest of which is more than 31 minutes. The results of examples such as this one could be useful in retrospective analyses, or if the signals were to serve as inputs to a predictive algorithm.

The calculated analyte concentrations are weighted and summed in order to minimize the squared error with respect to the extrinsically measured glucose concentration thereby creating the primary composite signal. FIG. 20 shows the primary composite signal superimposed on the individual temporally adjusted calculated analyte concentrations and the extrinsically measured glucose concentration.

What is claimed is:

1. A device for estimating the concentration of an analyte in a biological environment, said device comprising:
   (a) a housing;
   (b) at least two primary detectors disposed on the housing, wherein each primary detector is adapted to produce a signal responsive to the concentration of the analyte in the immediate biological microenvironment;
   (c) signal processing means in communication with each individual primary detector for receiving a signal therefrom and estimating the concentration of the analyte in the biological environment from the signals said signal processing means employing one or more predetermined algorithms, said signal processing means comprising:
   (i) means for adjusting the signals from each primary detector by applying signal adjustment coefficients thereto, wherein the coefficients compensate for detector failure, detector drift or variations between the biological microenvironments occupied by each detector;
   (ii) means for estimating the analyte concentration in the biological microenvironment of individual primary detectors; and
   (iii) means for estimating the concentration of the analyte by mathematical calculation of a primary composite signal indicative of said analyte concentration;
   (d) at least one secondary detector disposed on the housing, wherein each secondary detector is adapted to produce a signal responsive to one or more confounding phenomena in the biological microenvironment occupied by at least one primary detector;

(e) signal processing means in communication with each individual secondary detector for receiving a signal responsive to the presence of a confounding phenomenon in the biological microenvironment occupied by at least one primary detector, and a signal responsive to the magnitude of a confounding phenomenon in the biological microenvironment occupied by the secondary detector; and, (f) means for producing at least one secondary composite signal by adjusting detector signals from each secondary detector by applying signal adjustment coefficients thereto, wherein the coefficients have been selected to compensate for detector failure, detector drift, variations between biological microenvironments occupied by each secondary detector, and similarities between biological microenvironments occupied by secondary detectors and primary detectors with which they maybe associated.

2. A device for estimating the concentration of an analyte in a biological environment, said device comprising:
(a) a housing;
(b) at least two primary detectors disposed on the housing, wherein each primary detector is adapted to produce a signal responsive to the concentration of the analyte in the immediate biological microenvironment;
(c) signal processing means in communication with each individual primary detector for receiving a signal therefrom and estimating the concentration of the analyte in the biological environment from the signals said signal processing means employing one or more predetermined algorithms, said signal processing means comprising:
(i) means for adjusting the signals from each primary detector by applying signal adjustment coefficients thereto, wherein the coefficients compensate for detector failure, detector drift or variations between the biological microenvironments occupied by each detector;
(ii) means for estimating the analyte concentration in the biological microenvironment of individual primary detectors; and
(iii) means for estimating the concentration of the analyte by mathematical calculation of a primary composite signal indicative of said analyte concentration;
wherein the means for adjusting the signals from each primary detector applies weighting factors to determine the primary composite signal.

3. A device for estimating the concentration of an analyte in a biological environment, said device comprising:
(a) a housing;
(b) at least two primary detectors disposed on the housing, wherein each primary detector is adapted to produce a signal responsive to The concentration of the analyte in the immediate biological microenvironment;
(c) signal processing means in communication with each individual primary detector for receiving a signal therefrom and estimating the concentration of the analyte in the biological environment from the signals said signal processing means employing one or more predetermined algorithms, said signal processing means comprising:
(i) means for adjusting the signals from each primary detector by applying signal adjustment coefficients thereto, wherein the coefficients compensate for detector failure, detector drift or variations between the biological microenvironments occupied by each detector;
(ii) means for estimating the analyte concentration in the biological microenvironment of individual primary detectors; and
(iii) means for estimating the concentration of the analyte by mathematical calculation of a primary composite signal indicative of said analyte concentration;
wherein the means for adjusting the signals from each primary detector applies temporal factors to determine the primary composite signal.

4. A device for estimating the concentration of an analyte in a biological environment, said device comprising:
(a) a housing;
(b) at least two primary detectors disposed on the housing, wherein each primary detector is adapted to produce a signal responsive to the concentration of the analyte in the immediate biological microenvironment;
(c) signal processing means in communication with each individual primary detector for receiving a signal therefrom and estimating the concentration of the analyte in the biological environment from the signals said signal processing means employing one or more predetermined algorithms, said signal processing means comprising:
(i) means for adjusting the signals from each primary detector by applying signal adjustment coefficients thereto, wherein the coefficients compensate for detector failure, detector drift or variations between the biological microenvironment occupied by each detector;
(ii) means for estimating The analyte concentration in the biological microenvironment of individual primary detectors; and
(iii) means for estimating the concentration of the analyte by mathematical calculation of a primary composite signal indicative of said analyte concentration;
(d) at least one secondary detector disposed on the housing, wherein each secondary detector is adapted to produce a signal responsive to one or more confounding phenomena in the biological microenvironment occupied by at least one primary detector; and,
(e) signal processing means in communication with each individual secondary detector for receiving a signal responsive to the presence of a confounding phenomenon in the biological microenvironment occupied by at least one primary detector, and a signal responsive to the magnitude of a confounding phenomenon in the biological microenvironment occupied by the secondary detector;
wherein the means for adjusting the signals from each secondary detector applies weighting factors to determine a secondary composite signal.

5. A device for estimating the concentration of an analyte in a biological environment said device comprising:
(a) a housing;
(b) at least two primary detectors disposed on the housing, wherein each primary detector is adapted to produce a signal responsive to the concentration of the analyte in the immediate biological microenvironment;
(c) signal processing means in communication with each individual primary detector for receiving a signal therefrom and estimating the concentration of the analyte in the biological environment from the signals said signal processing means employing one or more predetermined algorithms, said signal processing means comprising:
(i) means for adjusting the signals from each primary detector by applying signal adjustment coefficients thereto, wherein the coefficients compensate for detector failure, detector drift or variations between the biological microenvironments occupied by each detector;

(ii) means for estimating the analyte concentration in the biological microenvironment of individual primary detectors; and (iii) means for estimating the concentration of the analyte by mathematical calculation of a primary composite signal indicative of said analyte concentration;

(d) at least one secondary detector disposed on the housing, wherein each secondary detector is adapted to produce a signal responsive to one or more confounding phenomena in the biological microenvironment occupied by at least one primary detector; and, (e) signal processing means in communication with each individual secondary detector for receiving a signal responsive to the presence of a confounding phenomenon in the biological microenvironment occupied by at least one primary detector, and a signal responsive to the magnitude of a confounding phenomenon in the biological microenvironment occupied by the secondary detector;

wherein the means for adjusting the signals from each secondary detector applies temporal factors to determine a secondary composite signal.

6. A device for estimating the concentration of an analyte in a biological environment, said device comprising:

(a) a housing;

(b) at least two primary detectors disposed on the housing, wherein each primary detector is adapted to produce a signal responsive to the concentration of the analyte in the immediate biological microenvironment;

(c) signal processing means in communication with each individual primary detector for receiving a signal therefrom and estimating the concentration of the analyte in the biological environment from the signals said signal processing means employing one or more predetermined algorithms, said signal processing means comprising:

(i) means for adjusting the signals from each primary detector by applying signal adjustment coefficients thereto, wherein the coefficients compensate for detector failure, detector drift or variations between the biological microenvironments occupied by each detector;

(ii) means for estimating the analyte concentration in the biological microenvironment of individual primary detectors; and (iii) means for estimating the concentration of the analyte by mathematical calculation of a primary composite signal indicative of said analyte concentration; and, (d) at least one secondary detector disposed on the housing, wherein each secondary detector is adapted to produce a signal responsive to one or more confounding phenomena in the biological microenvironment occupied by at least one primary detector;

wherein the at least one confounding phenomenon comprises the rate of perfusion of biological fluid.

7. A device for estimating the concentration of an analyte in a biological environment, said device comprising:

(a) a housing;

(b) at least two primary detectors disposed on the housing, wherein each primary detector is adapted to produce a signal responsive to the concentration of the analyte in the immediate biological microenvironment;

(c) signal processing means in communication with each individual primary detector for receiving a signal therefrom and estimating the concentration of the analyte in the biological environment from the signals said signal processing means employing one or more predetermined algorithms, said signal processing means comprising:

(i) means for adjusting the signals from each primary detector by applying signal adjustment coefficients thereto, wherein the coefficients compensate for detector failure, detector drift or variations between the biological microenvironments occupied by each detector;

(ii) means for estimating the analyte concentration in the biological microenvironment of individual primary detectors; and (iii) means for estimating the concentration of the analyte by mathematical calculation of a primary composite signal indicative of said analyte concentration; and, (d) at least one secondary detector disposed on the housing, wherein each secondary detector is adapted to produce a signal responsive to one or more confounding phenomena in the biological microenvironment occupied by at least one primary detector;

wherein the at least one confounding phenomenon comprises the rate of flow of biological fluid perfusing the biological environment.

8. A device for estimating the concentration of an analyte in a biological environment, said device comprising:

(a) a housing;

(b) at least two primary detectors disposed on the housing, wherein each primary detector is adapted to produce a signal responsive to the concentration of the analyte in the immediate biological microenvironment;

(c) signal processing means in communication with each individual primary detector for receiving a signal therefrom and estimating the concentration of the analyte in the biological environment from the signals said signal processing means employing one or more predetermined algorithms, said signal processing means comprising:

(i) means for adjusting the signals from each primary detector by applying signal adjustment coefficients thereto, wherein the coefficients compensate for detector failure, detector drift or variations between the biological microenvironment occupied by each detector;

(ii) means for estimating the analyte concentration in the biological microenvironment of individual primary detectors; and (iii) means for estimating the concentration of the analyte by mathematical calculation of a primary composite signal indicative of said analyte concentration, wherein the signal processing means utilizes predetermined algorithms including adjustment of detector signals according to weighting factors.

9. A device for estimating the concentration of an analyte in a biological environment, said device comprising:

(a) a housing;

(b) at least two primary detectors disposed on the housing, wherein each primary detector is adapted to produce a signal responsive to the concentration of the analyte in the immediate biological microenvironment;

(c) signal processing means in communication with each individual primary detector for receiving a signal therefrom and estimating the concentration of the analyte in the biological environment from the signals said signal processing means employing one or more predetermined algorithms, said signal processing means comprising:

(i) means for adjusting the signals from each primary detector by applying signal adjustment coefficients thereto, wherein the coefficients compensate for detector failure, detector drift or variations between the biological microenvironments occupied by each detector;

(ii) means for estimating the analyte concentration in the biological microenvironment of individual primary detectors; and (iii) means for estimating the concentration of the analyte by mathematical calculation of a primary composite signal indicative of said analyte concentration wherein the signal processing means utilizes predetermined algorithms including adjustment of detector signals according to temporal factors.

10. A device for estimating the concentration of an analyte in a biological environment, said device comprising:
  (a) a housing;
  (b) at least one primary detector disposed on the housing, wherein each primary detector is adapted to produce a signal responsive to the concentration of the analyte in the immediate biological microenvironment;
  (c) a plurality of secondary detectors disposed on the housing, wherein each secondary detector is adapted to produce a signal responsive to one or more confounding phenomena in the biological microenvironment of at least one primary detector; and,
  (d) signal processing means in communication with each individual detector for receiving a signal therefrom, said signal processing means comprising:
  (i) means for adjusting the signals from each secondary detector by applying signal adjustment coefficients thereto, wherein the coefficients compensate for detector failure, detector drift, variations between the biological microenvironments occupied by each detector, and confounding phenomena; and,
  (ii) means for estimating the analyte concentration in the biological microenvironment of each individual primary detector; and
  (iii) means for adjusting the estimated analyte concentration associated with each primary detector by applying signal adjustment coefficients thereto, wherein the coefficients compensate for detector failure, detector drift, variations between the biological microenvironments occupied by each detector, and confounding phenomena; and
  (iv) means for estimating the concentration of the analyte by mathematical calculation of a primary composite signal indicative of said analyte concentration;
  wherein the means for adjusting the estimated analyte concentration associated with each primary detector applies weighting factors to determine the primary composite signal.

11. A device for estimating the concentration of an analyte in a biological environment, said device comprising:
  (a) a housing;
  (b) at least one primary detector disposed on the housing, wherein each primary detector is adapted to produce a signal responsive to the concentration of the analyte in the immediate biological microenvironment;
  (c) a plurality of secondary detectors disposed on the housing, wherein each secondary detector is adapted to produce a signal responsive to one or more confounding phenomena in the biological microenvironment of at least one primary detector, and,
  (d) signal processing means in communication with each individual detector for receiving a signal therefrom, said signal processing means comprising:
  (i) means for adjusting the signals from each secondary detector by applying signal adjustment coefficients thereto, wherein the coefficients compensate for detector failure, detector drift, variations between to biological microenvironments occupied by each detector, and confounding phenomena; and,
  (ii) means for estimating to analyte concentration in the biological microenvironment of each individual primary detector, and
  (iii) means for adjusting the estimated analyte concentration associated with each primary detector by applying signal adjustment coefficients thereto, wherein the coefficients compensate for detector failure, detector drift, variations between the biological microenvironments occupied by each detector, and confounding phenomena; and
  (iv) means for estimating the concentration of the analyte by mathematical calculation of a primary composite signal indicative of said analyte concentration;
  wherein the means for adjusting the estimated analyte concentration associated with each primary detector applies temporal factors to determine the primary composite signal.

12. A device for estimating the concentration of an analyte in a biological environment, said device comprising:
  (a) a housing;
  (b) at least one primary detector disposed on the housing, wherein each primary detector is adapted to produce a signal responsive to the concentration of the analyte in the immediate biological microenvironment;
  (c) a plurality of secondary detectors disposed on the housing, wherein each secondary detector is adapted to produce a signal responsive to one or more confounding phenomena in the biological microenvironment of at least one primary detector; and,
  (d) signal processing means in communication with each individual detector for receiving a signal therefrom, said signal processing means comprising:
  (i) means for adjusting the signals from each secondary detector by applying signal adjustment coefficients thereto, wherein the coefficients compensate for detector failure, detector drift, variations between the biological microenvironments occupied by each detector, and confounding phenomena; and,
  (ii) means for estimating the analyte concentration in the biological microenvironment of each individual primary detector; and
  (iii) means for adjusting the estimated analyte concentration associated with each primary detector by applying signal adjustment coefficients thereto, wherein the coefficients compensate for detector failure, detector drift, variations between the biological microenvironments occupied by each detector, and confounding phenomena; and
  (iv) means for estimating the concentration of the analyte by mathematical calculation of a primary composite signal indicative of said analyte concentration;
  wherein the means for adjusting the signals from each secondary detector applies weighting factors to determine the secondary composite signal.

13. A device for estimating the concentration of an analyte in a biological environment, said device comprising:
  (a) a housing;
  (b) at least one primary detector disposed on the housing, wherein each primary detector is adapted to produce a signal responsive to the concentration of the analyte in the immediate biological microenvironment;
  (c) a plurality of secondary detectors disposed on the housing, wherein each secondary detector is adapted to produce a signal responsive to one or more confounding phenomena in the biological microenvironment of at least one primary detector; and, (d) signal processing means in communication with each individual detector for receiving a signal therefrom, said signal processing means comprising:
(i) means for adjusting the signals from each secondary detector by applying signal adjustment coefficients thereto, wherein the coefficients compensate for detector failure, detector drift, variations between the biological microenvironments occupied by each detector, and confounding phenomena; and,
(ii) means for estimating the analyte concentration in the biological microenvironment of each individual primary detector; and
(iii) means for adjusting the estimated analyte concentration associated with each primary detector by applying signal adjustment coefficients thereto, wherein the coefficients compensate for detector failure, detector drift, variations between the biological microenvironments occupied by each detector, and confounding phenomena; and
(iv) means for estimating the concentration of the analyte by mathematical calculation of a primary composite signal indicative of said analyte concentration;
wherein the means for adjusting the signals from each secondary detector applies temporal factors to determine the secondary composite signal.

14. A device for estimating the concentration of an analyte in a biological environment, said device comprising:
(a) a housing;
(b) at least one primary detector disposed on the housing, wherein each primary detector is adapted to produce a signal responsive to the concentration of the analyte in the immediate biological microenvironment;
(c) a plurality of secondary detectors disposed on the housing, wherein each secondary detector is adapted to produce a signal responsive to one or more confounding phenomena in the biological microenvironment of at least one primary detector; and,
(d) signal processing means in communication with each individual detector for receiving a signal therefrom, said signal processing means comprising:
(i) means for adjusting the signals from each secondary detector by applying signal adjustment coefficients thereto, wherein the coefficients compensate for detector failure, detector drift, variations between the biological microenvironments occupied by each detector, and confounding phenomena; and,
(ii) means for estimating the analyte concentration in the biological microenvironment of each individual primary detector; and
(iii) means for adjusting the estimated analyte concentration associated with each primary detector by applying signal adjustment coefficients thereto, wherein the coefficients compensate for detector failure, detector drift, variations between the biological microenvironments occupied by each detector, and confounding phenomena; and
(iv) means for estimating the concentration of the analyte by mathematical calculation of a primary composite signal indicative of said analyte concentration;
wherein the at least one confounding phenomenon comprises the rate of perfusion of biological fluid.

15. A device for estimating the concentration of an analyte in a biological environment, said device comprising:
(a) a housing;
(b) at least one primary detector disposed on the housing, wherein each primary detector is adapted to produce a signal responsive to the concentration of the analyte in the immediate biological microenvironment;
(c) a plurality of secondary detectors disposed on the housing, wherein each secondary detector is adapted to produce a signal responsive to one or more confounding phenomena in the biological microenvironment of at least one primary detector; and,
(d) signal processing means in communication with each individual detector for receiving a signal therefrom, said signal processing means comprising:
(i) means for adjusting the signals from each secondary detector by applying signal adjustment coefficients thereto, wherein the coefficients compensate for detector failure, detector drift, variations between the biological microenvironments occupied by each detector, and confounding phenomena; and,
(ii) means for estimating the analyte concentration in the biological microenvironment of each individual primary detector; and
(iii) means for adjusting the estimated analyte concentration associated with each primary detector by applying signal adjustment coefficients thereto, wherein the coefficients compensate for detector failure, detector drill, variations between the biological microenvironments occupied by each detector, and confounding phenomena; and
(iv) means for estimating the concentration of the analyte by mathematical calculation of a primary composite signal indicative of said analyte concentration;
wherein the at least one confounding phenomenon comprises the rate of flow of biological fluid perfusing the biological environment.

16. A device for estimating the concentration of an analyte in a biological environment, said device comprising:
(a) a housing;
(b) at least one primary detector disposed on the housing wherein each primary detector is adapted to produce a signal responsive to the concentration of the analyte in the immediate biological microenvironment;
(c) a plurality of secondary detectors disposed on the housing, wherein each secondary detector is adapted to produce a signal responsive to one or more confounding phenomena in the biological microenvironment of at least one primary detector; and,
(d) signal processing means in communication with each individual detector for receiving a signal therefrom, said signal processing means comprising;
(i) means for adjusting the signals from each secondary detector by applying signal adjustment coefficients thereto, wherein the coefficients compensate for detector failure, detector drift, variations between the biological microenvironments occupied by each detector, and confounding phenomena; and,
(ii) means for estimating the analyte concentration in the biological microenvironment of each individual primary detector; and
(iii) means for adjusting the estimated analyte concentration associated with each primary detector by applying signal adjustment coefficients thereto, wherein the coefficients compensate for detector failure, detector drift, variations between the biological microenvironments occupied by each detector, and confounding phenomena; and
(iv) means for estimating the concentration of the analyte by mathematical calculation of a primary composite signal indicative of said analyte concentration;
wherein the signal processing means utilizes predetermined algorithms including adjustment of detector signals according to temporal factors.

17. A device for estimating the concentration of an analyte in a biological environment, said device comprising:

(a) a housing;

(b) at least two primary detectors disposed on the housing, wherein each primary detector is adapted to produce a signal responsive to the concentration of the analyte in the immediate biological microenvironment;

(c) signal processing means in communication with each individual primary detector for receiving a signal therefrom and estimating the concentration of the analyte in the biological environment from the signals said signal processing means employing one or more predetermined algorithms, said signal processing means comprising:

(i) means for estimating the analyte concentration in the biological microenvironment of individual primary detectors;

(ii) means for adjusting the analyte concentration estimates by applying signal adjustment coefficients thereto, wherein the coefficients compensate for detector failure, detector drift or variations between the biological microenvironments occupied by each detector; and, (iii) means for estimating the concentration of the analyte by mathematical calculation of a primary composite signal indicative of said analyte concentration;

(d) at least one secondary detector disposed on the housing, wherein each secondary detector is adapted to produce a signal responsive to one or more confounding phenomena in the biological microenvironment occupied by at least one primary detector;

(e) signal processing means in communication with each individual secondary detector for receiving a signal responsive to the presence of a confounding phenomenon in the biological microenvironment occupied by at least one primary detector, and a signal responsive to the magnitude of a confounding phenomenon in the biological microenvironment occupied by the secondary detector; and, (f) means for producing at least one secondary composite signal by adjusting detector signals from each secondary detector by applying signal adjustment coefficients thereto, wherein the coefficients have been selected to compensate for detector failure, detector drift, variations between biological microenvironments occupied by each secondary detector, and similarities between biological microenvironments occupied by secondary detectors and primary detectors with which they may be associated.

18. A device for estimating the concentration of an analyte in a biological environment, said device comprising:

(a) a housing;

(b) at least two primary detectors disposed on the housing, wherein each primary detector is adapted to produce a signal responsive to the concentration of the analyte in the immediate biological microenvironment;

(c) signal processing means in communication with each individual primary detector for receiving a signal therefrom and estimating the concentration of the analyte in the biological environment from the signals said signal processing means employing one or more predetermined algorithms, said signal processing means comprising:

(i) means for estimating the analyte concentration in the biological microenvironment of individual primary detectors;

(ii) means for adjusting the analyte concentration estimates by applying signal adjustment coefficients thereto, wherein the coefficients compensate for detector failure, detector drift or variations between the biological microenvironments occupied by each detector; and, (iii) means for estimating the concentration of the analyte by mathematical calculation of a primary composite signal indicative of said analyte concentration;

wherein the means for adjusting the signals from each primary detector applies weighting factors to determine the primary composite signal.

19. A device for estimating the concentration of an analyte in a biological environment, said device comprising;

(a) a housing;

(b) at least two primary detectors disposed on the housing, wherein each primary detector is adapted to produce a signal responsive to the concentration of the analyte in the immediate biological microenvironment;

(c) signal processing means in communication with each individual primary detector for receiving a signal therefrom and estimating the concentration of the analyte in the biological environment from the signals said signal processing means employing one or more predetermined algorithms, said signal processing means comprising:

(i) means for estimating the analyte concentration in the biological microenvironment of individual primary detectors;

(ii) means for adjusting the analyte concentration estimates by applying signal adjustment coefficients thereto, wherein the coefficients compensate for detector failure, detector drift or variations between the biological microenvironments occupied by each detector; and, (iii) means for estimating the concentration of the analyte by mathematical calculation of a primary composite signal indicative of said analyte concentration;

wherein the means for adjusting the signals from each primary detector applies temporal factors to determine the primary composite signal.

20. A device for estimating the concentration of an analyte in a biological environment, said device comprising:

(a) a housing;

(b) at least two primary detectors disposed on the housing, wherein each primary detector is adapted to produce a signal responsive to the concentration of the analyte in the immediate biological microenvironment;

(c) signal processing means in communication with each individual primary detector for receiving a signal therefrom and estimating the concentration of the analyte in the biological environment from the signals said signal processing means employing one or more predetermined algorithms, said signal processing means comprising:

(i) means for estimating the analyte concentration in the biological microenvironment of individual primary detectors;

(ii) means for adjusting the analyte concentration estimates by applying signal adjustment coefficients thereto, wherein the coefficients compensate for detector failure, detector drift or variations between the biological microenvironments occupied by each detector; and, (iii) means for estimating the concentration of the analyte by mathematical calculation of a primary composite signal indicative of said analyte concentration;

(d) at least one secondary detector disposed on the housing, wherein each secondary detector is adapted to produce a signal responsive to one or more confounding phenomena in the biological microenvironment occupied by at least one primary detector; and, (e) signal processing means in communication with each individual secondary detector for receiving a signal responsive to the presence of a confounding phenomenon in the biological microenvironment occupied by at least one primary detector, and a signal responsive to the magnitude of a confounding phenomenon in the biological microenvironment occupied by the secondary detector;

wherein the means for adjusting the signals from each secondary detector applies weighting factors to determine a secondary composite signal.

21. A device for estimating the concentration of an analyte in a biological environment, said device comprising:
(a) a housing;
(b) at least two primary detectors disposed on the housing, wherein each primary detector is adapted to produce a signal responsive to the concentration of the analyte in the immediate biological microenvironment;
(c) signal processing means in communication with each individual primary detector for receiving a signal therefrom and estimating the concentration of the analyte in the biological environment from the signals said signal processing means employing one or more predetermined algorithms, said signal processing means comprising:
(i) means for estimating the analyte concentration in the biological microenvironment of individual primary detectors;
(ii) means for adjusting the analyte concentration estimates by applying signal adjustment coefficients thereto, wherein the coefficients compensate for detector failure, detector drift or variations between the biological microenvironments occupied by each detector; and,
(iii) means for estimating the concentration of the analyte by mathematical calculation of a primary composite signal indicative of said analyte concentration;
(d) at least one secondary detector disposed on the housing, wherein each secondary detector is adapted to produce a signal responsive to one or more confounding phenomena in the biological microenvironment occupied by at least one primary detector; and,
(e) signal processing means in communication with each individual secondary detector for receiving a signal responsive to the presence of a confounding phenomenon in the biological microenvironment occupied by at least one primary detector, and a signal responsive to the magnitude of a confounding phenomenon in the biological microenvironment occupied by the secondary detector;

wherein the means for adjusting the signals from each secondary detector applies temporal factors to determine a secondary composite signal.

22. A device for estimating the concentration of an analyte in a biological environment, said device comprising:
(a) a housing;
(b) at least two primary detectors disposed on the housing, wherein each primary detector is adapted to produce a signal responsive to the concentration of the analyte in the immediate biological microenvironment;
(c) signal processing means in communication with each individual primary detector for receiving a signal therefrom and estimating the concentration of the analyte in the biological environment from the signals said signal processing means employing one or more predetermined algorithms, said signal processing means comprising:
(i) means for estimating the analyte concentration in the biological microenvironment of individual primary detectors;
(ii) means for adjusting the analyte concentration estimates by applying signal adjustment coefficients thereto, wherein the coefficients compensate for detector failure, detector drift or variations between the biological microenvironments occupied by each detector; and,
(iii) means for estimating the concentration of the analyte by mathematical calculation of a primary composite signal indicative of said analyte concentration; and,
(d) at least one secondary detector disposed on the housing, wherein each secondary detector is adapted to produce a signal responsive to one or more confounding phenomena in the biological microenvironment occupied by at least one primary detector;

wherein the at least one confounding phenomenon comprises the rate of perfusion of biological fluid.

23. A device for estimating the concentration of an analyte in a biological environment, said device comprising:
(a) a housing;
(b) at least two primary detectors disposed on the housing, wherein each primary detector is adapted to produce a signal responsive to the concentration of the analyte in the immediate biological microenvironment;
(c) signal processing means in communication with each individual primary detector for receiving a signal therefrom and estimating the concentration of the analyte in the biological environment from the signals said signal processing means employing one or more predetermined algorithms, said signal processing means comprising:
(i) means for estimating the analyte concentration in the biological microenvironment of individual primary detectors;
(ii) means for adjusting the analyte concentration estimates by applying signal adjustment coefficients thereto, wherein the coefficients compensate for detector failure, detector drift or variations between the biological microenvironments occupied by each detector; and,
(iii) means for estimating the concentration of the analyte by mathematical calculation of a primary composite signal indicative of said analyte concentration; and,
(d) at least one secondary detector disposed on the housing, wherein each secondary detector is adapted to produce a signal responsive to one or more confounding phenomena in the biological microenvironment occupied by at least one primary detector;

wherein the at least one confounding phenomenon comprises the rate of flow of biological fluid perfusing the biological environment.

24. A device for estimating the concentration of an analyte in a biological environment, said device comprising:
(a) a housing;
(b) at least two primary detectors disposed on the housing, wherein each primary detector is adapted to produce a signal responsive to the concentration of the analyte in the immediate biological microenvironment;
(c) signal processing means in communication with each individual primary detector for receiving a signal therefrom and estimating the concentration of the analyte in the biological environment from the signals said signal processing means employing one or more predetermined algorithms, said signal processing means comprising:

(i) means for estimating the analyte concentration in the biological microenvironment of individual primary detectors;

(ii) means for adjusting the analyte concentration estimates by applying signal adjustment coefficients thereto, wherein the coefficients compensate for detector failure, detector drift or variations between the biological microenvironments occupied by each detector; and, (iii) means for estimating the concentration of the analyte by mathematical calculation of a primary composite signal indicative of said analyte concentration, wherein the signal processing means utilizes predetermined algorithms including adjustment of detector signals according to weighting factors.

25. A device for estimating the concentration of an analyte in a biological environment, said device comprising:
 (a) a housing;
 (b) at least two primary detectors disposed on the housing, wherein each primary detector is adapted to produce a signal responsive to the concentration of the analyte in the immediate biological microenvironment;
 (c) signal processing means in communication with each individual primary detector for receiving a signal therefrom and estimating the concentration of the analyte in the biological environment from the signals said signal processing means employing one or more predetermined algorithms, said signal processing means comprising:

(i) means for estimating the analyte concentration in the biological microenvironment of individual primary detectors;

(ii) means for adjusting the analyte concentration estimates by applying signal adjustment coefficients thereto, wherein the coefficients compensate for detector failure, detector drift or variations between the biological microenvironments occupied by each detector; and, (iii) means for estimating the concentration of the analyte by mathematical calculation of a primary composite signal indicative of said analyte concentration wherein the signal processing means utilizes predetermined algorithms including adjustment of detector signals according to temporal factors.

* * * * *